(12) United States Patent
Tripp et al.

(10) Patent No.: US 7,718,198 B2
(45) Date of Patent: *May 18, 2010

(54) TREATMENT MODALITIES FOR AUTOIMMUNE DISEASES

(75) Inventors: Matthew Tripp, Gig Harbor, WA (US); Jeffrey S. Bland, Fox Island, WA (US); Robert Lerman, Gig Harbor, WA (US); Amy Hall, Gig Harbor, WA (US); Veera Konda, Gig Harbor, WA (US); Anu Desai, Gig Harbor, WA (US)

(73) Assignee: Metaproteomics, LLC, San Clemente, CA (US)

( * ) Notice: Subject to any disclaimer, the term of this patent is extended or adjusted under 35 U.S.C. 154(b) by 78 days.

This patent is subject to a terminal disclaimer.

(21) Appl. No.: 11/326,874

(22) Filed: Jan. 6, 2006

(65) Prior Publication Data

US 2007/0020352 A1 Jan. 25, 2007

Related U.S. Application Data

(63) Continuation-in-part of application No. 10/866,315, filed on Jun. 10, 2004, which is a continuation-in-part of application No. 10/689,856, filed on Oct. 20, 2003, now Pat. No. 7,270,835, which is a continuation-in-part of application No. 10/464,410, filed on Jun. 18, 2003, which is a continuation-in-part of application No. 10/400,293, filed on Mar. 26, 2003, now abandoned, and a continuation-in-part of application No. 10/401,283, filed on Mar. 26, 2003, now abandoned, said application No. 10/866,315 is a continuation-in-part of application No. 10/464,834, filed on Jun. 18, 2003, and a continuation-in-part of application No. 09/885,721, filed on Jun. 20, 2001, now Pat. No. 7,205, 151.

(60) Provisional application No. 60/450,237, filed on Feb. 25, 2003, provisional application No. 60/420,383, filed on Oct. 21, 2002.

(51) Int. Cl.
*A01N 65/00* (2006.01)
(52) U.S. Cl. .................................................... 424/725
(58) Field of Classification Search .................. None
See application file for complete search history.

(56) References Cited

U.S. PATENT DOCUMENTS

| 2,175,340 | A | | 10/1939 | Chesney |
| 3,451,821 | A | * | 6/1969 | Todd, Jr. et al. ............... 426/16 |
| 3,552,975 | A | | 1/1971 | Worden et al. |
| 3,720,517 | A | | 3/1973 | Bavisotto et al. |
| 3,932,603 | A | | 1/1976 | Haas |
| 3,933,919 | A | | 1/1976 | Wilkinson |
| 3,965,188 | A | | 6/1976 | Westermann et al. |
| 4,123,561 | A | | 10/1978 | Grant |
| 4,133,903 | A | | 1/1979 | Thiele et al. |
| 4,148,873 | A | | 4/1979 | Owades |
| 4,154,865 | A | | 5/1979 | Grant |
| 4,170,638 | A | | 10/1979 | Owades |
| 4,401,684 | A | | 8/1983 | Versluys |
| 4,473,551 | A | | 9/1984 | Schinitsky |
| 4,554,170 | A | | 11/1985 | Panzer et al. |
| 4,644,084 | A | | 2/1987 | Cowles et al. |
| 4,692,280 | A | | 9/1987 | Spinelli |
| 4,767,640 | A | | 8/1988 | Goldstein et al. |
| 4,778,691 | A | | 10/1988 | Todd, Jr. et al. |
| 4,857,554 | A | | 8/1989 | Kallimanis |
| 4,956,195 | A | | 9/1990 | Todd, Jr. et al. |
| 5,006,337 | A | | 4/1991 | Motitschke et al. |
| 5,013,571 | A | | 5/1991 | Hay |
| 5,041,300 | A | | 8/1991 | Todd et al. |
| 5,073,396 | A | | 12/1991 | Todd, Jr. |
| 5,082,975 | A | | 1/1992 | Todd, Jr. et al. |
| 5,155,276 | A | | 10/1992 | Paul |
| 5,166,449 | A | | 11/1992 | Todd, Jr. et al. |
| 5,264,236 | A | | 11/1993 | Ogasahara et al. |
| 5,286,506 | A | | 2/1994 | Millis et al. |
| 5,296,637 | A | | 3/1994 | Ting et al. |
| 5,387,425 | A | | 2/1995 | Hsu et al. |
| 5,604,263 | A | | 2/1997 | Tobe et al. |
| 5,641,517 | A | | 6/1997 | Eskeland et al. |
| 5,827,895 | A | | 10/1998 | Nutter et al. |
| 5,968,539 | A | | 10/1999 | Beerse et al. |
| 6,020,019 | A | | 2/2000 | Ting et al. |

(Continued)

FOREIGN PATENT DOCUMENTS

DE 2212148 9/1972

(Continued)

OTHER PUBLICATIONS

The absolutely German Drink, 2003.*

(Continued)

*Primary Examiner*—Michael V Meller
(74) *Attorney, Agent, or Firm*—McDermott Will & Emery, LLP

(57) ABSTRACT

Compositions of reduced isoalpha acids, vitamins and minerals are disclosed as well as methods of using the same for the treatment of autoimmune diseases. Additional combinations including other compounds are also contemplated. Synergistic properties and methods exploiting such synergy are also disclosed.

8 Claims, 3 Drawing Sheets

U.S. PATENT DOCUMENTS

| | | | |
|---|---|---|---|
| 6,129,907 | A | 10/2000 | Sreenivasan et al. |
| 6,200,594 | B1 | 3/2001 | Ernest et al. |
| 6,383,527 | B1 | 5/2002 | Artman et al. |
| 6,391,346 | B1 | 5/2002 | Newmark et al. |
| 6,440,465 | B1 | 8/2002 | Meisner |
| 6,447,762 | B1 | 9/2002 | Galcerá |
| 6,583,322 | B1 | 6/2003 | Shalai et al. |
| 6,801,860 | B1 | 10/2004 | Dessen et al. |
| 2002/0076452 | A1 | 6/2002 | Babish et al. |
| 2002/0077299 | A1 | 6/2002 | Babish et al. |
| 2002/0086062 | A1 | 7/2002 | Kuhrts |
| 2002/0086070 | A1 | 7/2002 | Kuhrts |
| 2003/0077313 | A1 | 4/2003 | Schwartz et al. |
| 2003/0096027 | A1 | 5/2003 | Babish et al. |
| 2003/0113393 | A1 | 6/2003 | Babish et al. |
| 2003/0133958 | A1 | 7/2003 | Kuno et al. |
| 2004/0072900 | A1 | 4/2004 | Artman et al. |
| 2004/0086580 | A1 | 5/2004 | Tripp et al. |
| 2004/0137096 | A1 | 7/2004 | Kuhrts |
| 2004/0151792 | A1 | 8/2004 | Tripp et al. |
| 2004/0219240 | A1 | 11/2004 | Babish et al. |

FOREIGN PATENT DOCUMENTS

| | | |
|---|---|---|
| DE | 3931147 | 3/1991 |
| DE | 19841615 | 3/2000 |
| JP | 63211219 | 9/1988 |
| JP | 4202138 | 7/1992 |
| JP | 6312924 | 11/1994 |
| JP | 07194351 | 8/1995 |
| JP | 8073369 | 3/1996 |
| JP | 409067245 | 3/1997 |
| JP | 10025247 | 1/1998 |
| JP | 10152428 | 6/1998 |
| RU | 2045995 | 10/1995 |
| SU | 1247011 | 7/1986 |
| WO | WO99/44623 | 9/1999 |
| WO | WO 00/68356 | 11/2000 |
| WO | WO00/74696 | 12/2000 |
| WO | WO02/02582 | 1/2002 |

OTHER PUBLICATIONS

See sheet Nos. 4-5.
"Information on arthrotrimtm product", downloaded from Internet Aug. 30, 2002.
"Information on Zyflamend and Zyflamend PM", downloaded from Internet Aug. 30, 2002.
"Information on Hops and Beer Flavours", downloaded from internet Feb. 15, 2005.
Anto, et al. Pharm. Pharmacol. Comm. 4:103-106 (1998).
Bermejo, et al. Rev. Esp. Enferm. Dig. 95: 621-624 and 625-628 (2003).
Brown, et al. J. Chem. Soc. 545 (1959).
Byrne, et al. J. Chem. Soc. (c):2810 (1971).
Carroccio, et al. Clin. Chem. 49:861-867 (2003).
Carson, j. Am. Chem. Soc. 73:1850-1851 (1951).
Chandra, et al. Indian J. Medical Research 60(1):138-142 (1972).
Charlier, et al. Eur. J. Med. Chem. 38:645-659 (2003).
Chou et al. Eur. J. Biochem. 115:207-216 (1981).
Chou, et al. Adv enzyme regul 22:27-55 (1984).
Chou, et al. J. Biol. Chem. 252:6438-6442 (1977).
Chou, et al. J. Theor. Biol. 35:285-297 (1972).
Chou, et al. Trends Pharm. Sci. 4:450-454 (1983).
Chou, j. Theor. Biol. 59:253-276 (1976).
Costa, et al. Digest. Liver Dis. 35:642-647 (2003).
Davies, WL. Abstract—Fertiliser, Feeding stuffs and Farm Supplies J. 11:694 (1926).
Ding, et al. Biochem. Biophy. Res. Comm. 261:218-223 (1999).
Friedman, et al. J Cutan Med. Surg. 6(5):449-459 (2002).
Germany, "The Absolutely German Drink," contents of beer, 2004, 5 pages.
Goldstein, et al. Am. J. Gastroenterol. 96:1019-1027 (2001).
Halter, et al. Gut 49:443-453 (2001).
Hamberg, et al. J. Bio. Chem. 246:6713-6721 (1971).
Huang, et al. Cancer Res. 51:813-819 (1991).
International Search Report for PCT/US02/19617.
International Search Report for PCT/US04/16043.
Jach, Przegl Dermatol. 65(4):379-382 (1978).
Kanematsu, et al. J Bone Miner Res 12(11):1789-1796 (1997).
Lopes, Curr. Med Res Opin. 8:145-149 (1982).
Meling, et al. Scand. J. Gastroenterol. 31:339-344 (1996).
Noreen, et al. J. Nat. Prod 61:2-7 (1998).
Pairet, et al. Inflamm. Res 47, Supplement 2s93-s101 (1998).
Panglisch, monafsschrift fuer brauwissen schaft, 1990, 43(1), 4-16.
Pippa, et al. Scand. J. Gastroenterol. Suppl. 167:32-35 (1989).
Plewig, et al. J Invest. Dermatol. 65(6):532-536 (1975).
Poullis, et al. J. Gastroenterol. Hepatol. 18:756-762 (2003).
Ringbom, et al. J. Nat Prod 61:1212-1215 (1998).
Røseth, digest. Liver Dis. 35:607-609 (2003).
Schjerven, et al. Br. J. Dermatol. 149:484-491 (2003).
Shah, et al. Gut 48:339-346 (2001).
Shimamura, et al. Biochem. Biophys. Res. Comm. 289:220-224 (2001).
Shureiqi, et al. Cancer res. 61:6307-6312 (2001).
Sivri, fundam. Clinic. Pharmacol. 18:23-31 (2004).
Subbaramaiah, et al. Cancer Res. 60:2399-2404 (2000).
Suh, et al. Cancer Res. 58:717-723 (1988).
Tagashira, et al., Biosci. Biotech. Biochem. 59(4):740-742 (1996).
Thomas m. Newmark and paul schulick, Beyond Aspirin nature's answer to arthritis, cancer & alzheimer's disease, hohm press (2000) release 7; pp. 147-151, 248.
Tibble, et al. Drugs Today 37:85-96 (2001).
Tibble, et al. Gut 45:362-366 (1999).
Tobe, et al. Biosci. Biotech. Biochem 61(1):158-159 (1997).
Wang, et al. Free Radical Biology & Medicine 27:612-616 (1999).
Warner, et al. Proc Natl Acad Sci USA 96:7563-7568 (1999).
Yamamoto, et al. Abstract—Prostaglandins & Other Lipid Mediators 59:1-235 (1999).
Yamamoto, FEBS Letters 465:103-106 (2000).
Yui, et al. Biol. Pharm. Bull. 26:753-760 (2003).
International Search Report of corresponding PCT Application S/N: PCT/US07/00137, 2 pp.
Written Opinion of corresponding PCT Application S/N: PCT/US07/00137, 4 pp.
About.Com, Beer Nutrition, 3 pp, downloaded from internet Oct. 20, 2008.

* cited by examiner

[A]

[B]

[C]

[D]

[E]

TREATMENT MODALITIES FOR AUTOIMMUNE DISEASES

CROSS-REFERENCE TO RELATED APPLICATIONS

This patent application is a continuation-in-part of U.S. application Ser. No. 10/866,315, filed Jun. 10, 2004, which is a continuation-in-part of U.S. application Ser. No. 10/689,856, filed Oct. 20, 2003, now U.S. Pat. No. 7,270,835, which is a continuation-in-part of U.S. application Ser. No. 10/464,410, filed Jun. 18, 2003, which is a continuation-in-part of U.S. application Ser. No. 10/400,293, filed Mar. 26, 2003 (abandoned), and a continuation-in-part of U.S. application Ser. No. 10/401,283, filed Mar. 26, 2003 (abandoned), both of which claim the benefit under 35 U.S.C. §119(e) to provisional application No. 60/450,237, filed on Feb. 25, 2003, and provisional application No. 60/420,383, filed on Oct. 21, 2002; and is a continuation-in-part of U.S. patent application Ser. No. 10/464,834, filed Jun. 18, 2003, which is a continuation-in-part of U.S. application Ser. No. 10/400,293, filed Mar. 26, 2003 abandoned, and a continuation-in-part of U.S. application Ser. No. 10/401,283, filed Mar. 26, 2003 (abandoned), both of which claim the benefit under 35 U.S.C. §119(e) to provisional application No. 60/450,237, filed on Feb. 25, 2003, and provisional application No. 60/420,383, filed on Oct. 21, 2002. This application is also a continuation-in-part of U.S. application Ser. No. 09/885,721, filed Jun. 20, 2001, now U.S. Pat. No. 7,205,151. The contents of each of these earlier applications are hereby incorporated by reference as if recited herein in their entirety.

BACKGROUND OF THE INVENTION

1. Field of the Invention

The present invention relates generally to compositions and methods useful to treat autoimmune diseases. More specifically, the invention relates to compositions of reduced isoalpha acids, minerals and vitamins.

2. Description of the Related Art

Autoimmune diseases and disorders occur when the body's own protective immune system becomes self destructive. The targets of autoimmune interaction can range anywhere from the cellular level (e.g., myelin basic protein in multiple sclerosis, or the thyrotropin receptor in Graves' disease) to organ specific effects in rheumatoid arthritis or Crohn's disease to system wide effects as seen in systemic lupus erythematosus. Some of the events that have been postulated in the causation of autoimmune diseases have included cytokine over expression, for example TNF-α, IL-2, or IL-2 receptor in inflammatory bowel disease, or under expression (IL-10 under expression in Type 1 diabetes), to defects in allele expression (HLA Class I B27 in ankylosing spondylitis), to altered expression of apoptosis proteins (under expression of Fas in autoimmune lymphoproliferative syndrome type 1 (ALPS 1). See Harrison's *Principles of Internal Medicine*, 16th ed., McGraw-Hill, New York, 2005; Chapter 295 for additional information on autoimmune diseases.

Inflammation, while not causative of many autoimmune diseases, none the less is a symptom often associated with autoimmune diseases and disorders, such as, for example, rheumatoid arthritis, inflammatory bowel disease, Crohn's disease, or ulcerative colitis. As such, anti-inflammatory agents are often incorporated into many autoimmune treatment modalities as a means of palliative relief.

Compounds that inhibit the production of prostaglandin (PG)s have become important drugs in the control of pain and inflammation. Collectively these agents are known as non-steroidal anti-inflammatory drugs (NSAIDs) with their main indications being osteoarthritis and rheumatoid arthritis. Arachidonic acid serves as the primary substrate for the biosynthesis of all PGs. PGs are ubiquitous hormones that function as both paracrine and autocrine mediators to affect a myriad of physiological changes in the immediate cellular environment. The varied physiological effects of PGs include inflammatory reactions such as in rheumatoid arthritis and osteoarthritis, blood pressure control, platelet aggregation, induction of labor and aggravation of pain and fever.

In addition to prostaglandins, recent research has shown that trace metal levels of zinc and selenium may have a possible role in the etiology and pathogenesis of osteoarthritis and rheumatoid arthritis. Plasma and synovial fluid Se concentration were found to be significantly lower ($p<0.05$, and $p<0.05$, respectively), whereas Cu concentrations were significantly higher in patients with rheumatoid arthritis than those of healthy subjects. The investigators additionally identified a significantly positive correlation between synovial fluid Se—Cu values and Zn—Fe values in patients with rheumatoid arthritis (see Yazar, M., et al., Biol. Trace Elem Res 106(2): 123-132, 2005; McConnell, K. P., et al., J. Nutr. 105(8): 1026-1031, 1975). This suggests that trace metal supplementation may be advantageous in ameliorating some of the symptoms associated with rheumatoid arthritis by bringing those trace element levels to a more normal level.

Further, it has long been known that the macrophage is a potent mediator of immune reactions and that rheumatoid arthritis is characterized by a migration of activated phagocytes (and other immunoreactive cells) into synovial and periarticular tissue. The activated phagocytes, upon reaching the synovia release numerous mediating substances that appear to both exacerbate and perpetuate the rheumatoid condition. Pharmacological doses of zinc may immobilize macrophages, thereby preventing or limiting their access to the synovial site and providing a potential means to reduce joint specific inflammation in rheumatoid arthritis. See, for example, Aaseth, J., et al., Analyst 123(1): 3-6, 1998). Additionally, macrophage immobilization may play a role in reducing macrophage interaction and activation, thereby reducing possible participation in, or augmentation of, the autoimmune response.

Therefore, it would be useful to identify compositions and methods that would modulate prostaglandin levels and or regulate macrophage activity, thereby modulating the inflammatory response associated with many autoimmune diseases. Such modulation and use may require continual use for chronic conditions or intermittent use as needed. Additionally, supplementation with select trace metals may also serve a means towards restoring a more normal immune function, thereby offering an additional avenue for intervention in autoimmune diseases. The instant invention describes compounds, compositions and methods to treat inflammation and autoimmune diseases related symptoms with a concomitant increase in the quality of life.

SUMMARY OF THE INVENTION

The invention relates to novel modalities useful for the treatment of inflammation and autoimmune diseases and related symptoms with a concomitant increase in the quality of life.

An aspect of the invention relates to compositions comprising a reduced isoalpha acid compound, a mineral, and a vitamin. Reduced isoalpha acid compounds contemplated include dihydro-isohumulone, dihydro-isocohumulone, dihydro-isoadhumulone, tetrahydro-isohumulone tetrahydro-isocohumulone, tetrahydro isoadhumulone, hexahydro-isohumulone, hexahydro-isocohumulone, and hexahydro-isoadhumulone. Reduced isoalpha acids also encompass moieties also known as "rho" isoalpha acids.

In another aspect, the invention also provides methods of using such compositions for the treatment of autoimmune diseases. In this aspect of the invention, a mammal may be treated by the administration of a therapeutically effective amount of a composition including a reduced isoalpha acid compound, a mineral, and a vitamin. Reduced isoalpha acid compounds contemplated include dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. Reduced isoalpha acids also encompass moieties also known as "rho" isoalpha acids.

DETAILED DESCRIPTION OF THE PREFERRED EMBODIMENT

Figure 1:
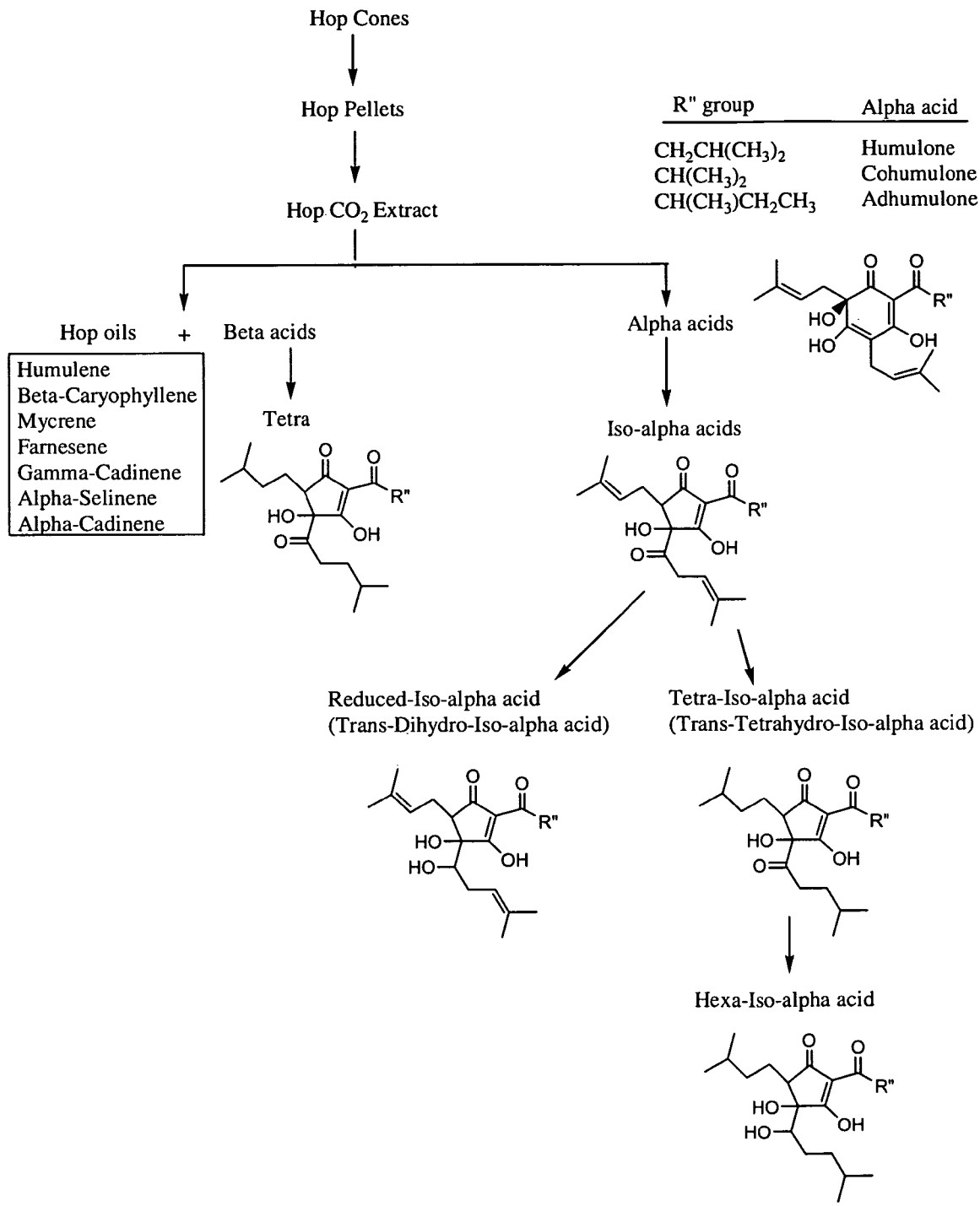
FIG. 1 shows an outline of fractions and compounds obtained from hops.

The present invention relates to the identification of compositions combining a reduced isoalpha acid, a mineral, and a vitamin which have been found to be effectual in the treatment of autoimmune diseases.

An aspect of the invention relates to compositions comprising one ore more of each of (i) a reduced isoalpha acid compound, (ii) a mineral, and (iii) a vitamin.

In the specification and the appended claims, the singular forms include plural referents unless the context clearly dictates otherwise. As used in this specification, the singular forms "a," "an" and "the" specifically also encompass the plural forms of the terms to which they refer, unless the content clearly dictates otherwise. As used herein, unless specifically indicated otherwise, the word "or" is used in the "inclusive" sense of "and/or" and not the "exclusive" sense of "either/or." As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of medicine include Harrison's *Principles of Internal Medicine*, 16th ed., McGraw-Hill, New York, 2005. Standard reference works setting forth the general principles of pharmacology include Goodman and Gilman's *The Pharmacological Basis of Therapeutics*, 10th Ed., McGraw Hill Companies Inc., New York (2001).

The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

The term "reduced isoalpha acid" refers to alpha acids isolated from hops plant product and subsequently have been isomerized and reduced, including cis and trans forms. Examples of reduced isoalpha acids ("RIAA") include, but are not limited to dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone.

As used herein, the term "tetra-hydroisoalpha acid" refers to a certain class of reduced isoalpha acid. Examples of tetrahydroisoalpha acid ("THIAA") include, but are not limited to, tetra-hydro-isohumulone, tetra-hydro-isocohumulone and tetra-hydro-isoadhumulone. As used herein, the term "hexa-hydroisoalpha acid" refers to a certain class of reduced isoalpha acid. Examples of hexa-hydroisoalpha acids ("HHIAA") include, but are not limited to, hexa-hydro-isohumulone, hexa-hydro-isocohumulone and hexa-hydro-isoadhumulone.

Reduced isoalpha acid compounds according to the invention may be synthesized or may be obtained as fractions or compounds isolated, extracted, derived from hops or spent hops (see Verzele, M. and De Keukeleire, D., *Developments in Food Science* 27: *Chemistry and Analysis of Hop and Beer Bitter Acids*, Elsevier Science Pub. Co., 1991, New York, USA, herein incorporated by reference in its entirety, for a detailed discussion of hops chemistry).

As used herein, the term "hop extract" refers to the solid material resulting from (1) exposing a hops plant product to a solvent, (2) separating the solvent from the hops plant products, and (3) eliminating the solvent. As used herein, the term "solvent" refers to a liquid of aqueous or organic nature possessing the necessary characteristics to extract solid material from the hop plant product. Examples of solvents would include, but not limited to, water, steam, superheated water, methanol, ethanol, hexane, chloroform, liquid $CO_2$, liquid $N_2$ or any combinations of such materials. As used herein, the term "$CO_2$ extract" refers to the solid material resulting from exposing a hops plant product to a liquid or supercritical $CO_2$ preparation followed by removing the $CO_2$. As used herein, the term "spent hops" refers to the solid and hydrophilic residue from extract of hops.

Reduced isoalpha acids also encompass moieties also known as "rho" isoalpha acids. Compositions thus, may include rho isoalpha acid compounds. As used herein, "rho" refers to those reduced isoalpha acids wherein the reduction is a reduction of the carbonyl group in the 4-methyl-3-pentenoyl side chain. This subset of reduced isoalpha acids encompass any compound which is part of the supragenus structure shown below:

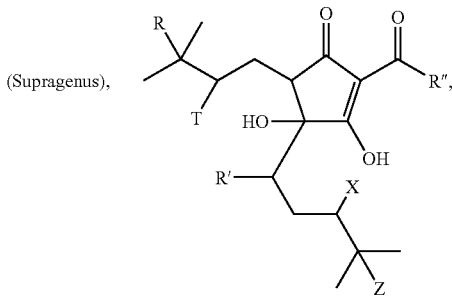
(Supragenus), wherein R' is selected from the group consisting of carbonyl, hydroxyl, OR, and OCOR, wherein R is alkyl; wherein R" is selected from the group consisting of $CH(CH_3)_2$, $CH_2CH(CH_3)_2$, and $CH(CH_3)CH_2CH_3$; and wherein R, T, X, and Z are independently selected from the group consisting of H, F, Cl, Br, I, and π orbital, with the proviso that if one of R, T, X, or Z is a π orbital, then the adjacent R, T, X, or Z is also a π orbital, thereby forming a double bond.

Certain embodiments of the invention include one or more reduced alpha acid compounds which fall within the scope of the Genus A structure:

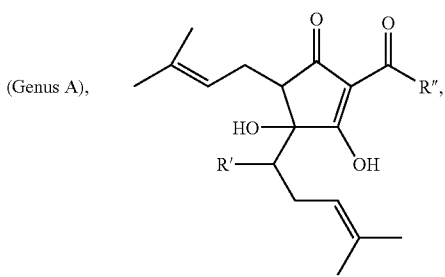
(Genus A), wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

Reduced isoalpha acid compounds also include compounds within the scope of the Genus B structure:

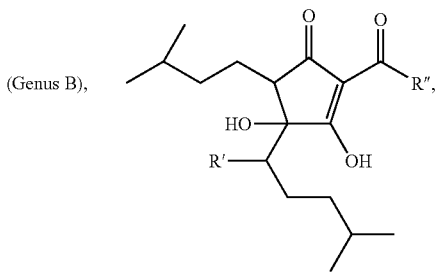
(Genus B), wherein R' is selected from the group consisting of carbonyl, hydroxyl, OR, and OCOR, wherein R is alkyl; and wherein R" is selected from the group consisting of $CH(CH_3)_2$, $CH_2CH(CH_3)_2$, and $CH(CH_3)CH_2CH_3$.

Minerals useful according to the invention include calcium, selenium, zinc, copper, iron, chromium, magnesium, manganese, vanadium, molybdenum, and boron. In certain non-limiting examples shown herein, the minerals are zinc and selenium.

Vitamins useful according to the invention include Vitamin A, Vitamin B, Vitamin C, Vitamin D, Vitamin E, Vitamin K, biotin, folate, pantothenic acid, para-aminobenzoic acid, and betaine. In certain non-limiting examples shown herein, the vitamin is vitamin D.

Compositions of the invention may include (a) one or more reduced isoalpha acid (dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone), (b) one or more rho reduced isoalpha acid compound of the Supragenus having the formula as shown and as described above; as well as (c) a vitamin, and (d) a mineral. In certain embodiments, the rho reduced isoalpha acid compound is part of the Genus A having the formula as shown and as described above. In yet additional embodiments, the rho reduced isoalpha acid compound is part of the Genus B having the formula as shown and as described above. The minerals and vitamins for these compositions are as described above. In representative non limiting embodiments of the invention exemplified herein, the minerals are zinc and selenium and the vitamin is vitamin D.

Other embodiments relate to compositions including additional components which may further benefit a patient. Thus, compositions of the invention may further include at least one member selected from the group consisting of rosemary, an extract or compound derived from rosemary, a triterpene species or derivatives or conjugates thereof, a diterpene lactone species or derivatives or conjugates thereof, and tryptanthrin or conjugates thereof. As used herein, the terms "derivatives" or a matter "derived" refer to a chemical substance related structurally to another substance and theoretically obtainable from it, i.e., a substance that can be made from another substance. Derivatives can include compounds obtained via a chemical reaction. The terms "conjugates" of compounds means compounds covalently bound or conjugated to a member selected from the group consisting of mono- or di-saccharides, amino acids, sulfates, succinate, acetate, and glutathione. Preferably, the mono- or di-saccharide is a member selected from the group consisting of glucose, mannose, ribose, galactose, rhamnose, arabinose, maltose, and fructose.

The amount of reduced isoalpha acid compound(s) in the compositions may be from about 0.5 to about 10,000 mg. In certain embodiments, the reduced isoalpha acid compound amount is from about 50 to about 7,500 mg. In certain embodiments exemplified herein, the unit dose comprises 225 mg of reduced isoalpha acids, 500 IU of vitamin D (as cholecalciferol), 5 mg of zinc (as zinc citrate) and 50 µg of selenium (as selenomethionine). As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compositions according to the invention may further comprise a pharmaceutically acceptable carrier. Any suitable materials and/or methods known to those of skill can be utilized in carrying out the present invention. However, preferred materials and methods are described. Materials, reagents and the like to which reference is made in the following description and examples are obtainable from commercial sources, unless otherwise noted.

The compounds according to the invention are optionally formulated in a pharmaceutically acceptable vehicle with any of the well known pharmaceutically acceptable carriers, including diluents and excipients (see *Remington's Pharmaceutical Sciences*, 18$^{th}$ Ed., Gennaro, Mack Publishing Co., Easton, Pa. 1990 and *Remington: The Science and Practice of Pharmacy*, Lippincott, Williams & Wilkis, 1995). While the type of pharmaceutically acceptable carrier/vehicle employed in generating the compositions of the invention will vary depending upon the mode of administration of the composition to a mammal, generally pharmaceutically acceptable carriers are physiologically inert and non-toxic. Formulations of compositions according to the invention may contain more than one type of compound of the invention), as well any other pharmacologically active ingredient useful for the treatment of the symptom/condition being treated.

As used herein, the term "composition" include any and all possible compositions suitable for the administration of the combinations encompassed by the invention and thus include for example dietary supplement compositions and generally neutraceutical as well as pharmaceutical compositions.

The compositions and methods of using the same according to the inventions have been found to be effective in the inhibition of $PGE_2$. Thus, the invention provides compositions and methods of inhibiting $PGE_2$. Without wishing to be bound by any one mechanism of action, applicants postulate that these compositions and methods are effective in the treatment of inflammation and autoimmune disease by a $PGE_2$ mediated mechanism. Accordingly, the compositions of the invention are believed to modulate prostaglandin levels and or regulate macrophage activity, thereby modulating the inflammatory response associated with autoimmune diseases.

In another aspect, the invention also provides methods of using such compositions for the treatment of inflammation and autoimmune diseases and related symptoms in a patient with a concomitant increase in the quality of life.

As used herein, "autoimmune disorder" refers to those diseases, illnesses, or conditions engendered when the host's systems are attacked by the host's own immune system. Representative, non-limiting examples of autoimmune diseases include alopecia areata, ankylosing spondylitis, arthritis, antiphospholipid syndrome, autoimmune Addison's disease, autoimmune hemolytic anemia, autoimmune inner ear disease (also known as Meniers disease), autimmune lymphoproliferative syndrome (ALPS), autoimmune thrombocytopenic purpura, autoimmune hemolytic anemia, autoimmune hepatitis, Bechet's disease, Crohn's disease, diabetes mellitus type 1, glomerulonephritis, Graves' disease, Guillain-Barré syndrome, inflammatory bowel disease, lupus nephritis, multiple sclerosis, myasthenis gravis, pemphigus, pernicous anemia, polyarteritis nodosa, polymyositis, primary billiary cirrhosis, psoriasis, Raynaud's Phenomenon, rheumatic fever, rheumatoid arthritis, scleroderma, Sjögren's syndrome, systemic lupus erythematosus, ulcerative colitis, vitiligo, and Wegener's granulamatosis.

The methods of the present invention are intended for use with any mammal that may experience the benefits of the methods of the invention. Foremost among such mammals are humans, although the invention is not intended to be so limited, and is applicable to veterinary uses. Thus, in accordance with the invention, "mammals" or "mammal in need" include humans as well as non-human mammals, particularly domesticated animals including, without limitation, cats, dogs, and horses.

In this aspect of the invention, a mammal may be treated by the administration of a therapeutically effective amount of a composition including a reduced isoalpha acid compound, a mineral, and a vitamin.

Compositions useful for the treatment according to this aspect of the invention encompass compositions comprising one ore more of each of (i) a reduced isoalpha acid compound, (ii) a mineral, and (iii) a vitamin.

Compositions useful for the methods of the invention may comprise rho reduced isoalpha acids of Supragenus structure as described and as shown above for the first aspect of the invention. Similarly, compositions may comprise reduced isoalpha acids of Genus A and/or Genus B as described and as having the formulae shown above for the first aspect of the invention.

Compositions suitable according to the methods of the invention may include (a) one or more reduced isoalpha acid (dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone), (b) one or more rho reduced isoalpha acid compound of the Supragenus having the formula as shown and as described above; as well as (c) a vitamin, and (d) a mineral. In certain embodiments, the rho reduced isoalpha acid compound is part of the Genus A having the formula as shown and as described above. In yet additional embodiments, the rho reduced isoalpha acid compound is part of the Genus B having the formula as shown and as described above. The minerals and vitamins for these compositions are as described above. In representative non limiting embodiments of the invention exemplified herein, the minerals are zinc and selenium and the vitamin is vitamin D.

Other embodiments relate to methods for the administration of compositions including additional components which may further benefit a patient. Thus, compositions of the invention may further include at least one member selected from the group consisting of rosemary, an extract or compound derived from rosemary, a triterpene species or derivatives or conjugates thereof, a diterpene lactone species or derivatives or conjugates thereof, and tryptanthrin or conjugates thereof. For a description of rosemary extract, compounds derived from rosemary, triterpene species (including derivatives or conjugates thereof), diterpene lactone species or derivatives or conjugates thereof, and tryptanthrin or conjugates thereof see e.g., U.S. patent application Ser. No. 10/689,856 hereby incorporated in its entirety.

As used herein, the term "effective amount" means an amount necessary to achieve a selected result. Such an amount can be readily determined without undue experimentation by a person of ordinary skill in the art. As used herein, the term "substantial" means being largely but not wholly that which is specified.

While not wishing to be bound by theory, the present inventors believe that the combinations contemplated herein may function to inhibit prostaglandin release selectively. Prostaglandin inhibition by the instant compositions is postulated to result in the down regulation of inflammation.

Figure 3:
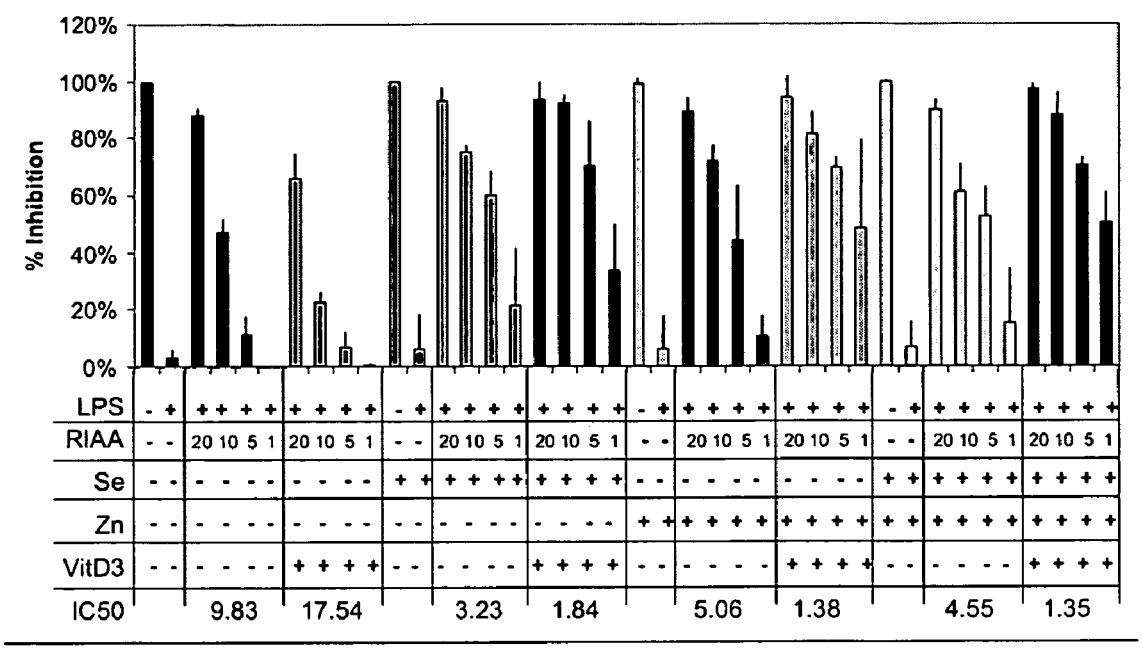
FIG. 3 is a graphical representation showing the inhibition of PGE2 secretion in LPS stimulated RAW 264.7 cells by various combinations of reduced isoalpha acids ("RIAA"), vitamin D, zinc and selenium.

As exemplified hereinafter, the compositions of the invention have been found too produce a synergistic effect as exemplified in FIG. 3 infra. As employed herein, the terms "synergy" and "synergistic effect" indicate that the effect produced from the aggregate compounds administered in toto is greater than would be predicted based on the effects produced when combinations of compounds less than the total aggregate are co-administered.

The selected dosage level will depend upon activity of the particular composition, the route of administration, the severity of the condition being treated or prevented, and the condition and prior medical history of the patient being treated. However, it is within the skill of the art to start doses of the composition at levels lower than required to achieve the desired therapeutic effect and to gradually increase the dosage until the desired effect is achieved. If desired, the effective daily dose may be divided into multiple doses for purposes of administration, e.g., two to four separate doses per day. It will be understood, however, that the specific dose level for any particular patient will depend upon a variety of factors including body weight, general health, diet, time and route of administration, combination with other compositions and the severity of the particular condition being treated or prevented.

Certain embodiments include delivering an effective amount of a reduced isoalpha acid with other active ingredients. Preferably, a daily dose of preferred compositions would be formulated to deliver about 0.5 to 10,000 mg of reduced isoalpha acid per day. More preferably, an effective daily dose of preferred compositions would be formulated to deliver about 50 to 7,500 mg of reduced isoalpha acid per day. Preferably, the effective daily dose is administered once or twice a day. Daily dosages of from about 0.5 to about 800 mg of reduced isoalpha acid, more preferably about 50 to 400 mg of reduced isoalpha acid per day are contemplated by the inventors. Another certain embodiment provides a composition comprising about 10 to 3,000 mg of reduced isoalpha acid per day, more preferably about 50 to 2,000 mg of reduced isoalpha acid per day.

Preferred embodiments include delivering an effective amount of tryptanthrin or conjugates thereof alone or with in combination with other active ingredients. Preferably, a daily dose of preferred compositions would be formulated to deliver about 0.0005 to 50 mg tryptanthrin/kg body weight per day. More preferably, an effective daily dose of preferred compositions would be formulated to deliver about 0.01 to 10 mg tryptanthrin/kg body weight per day. Preferably, a daily dose of preferred compositions would be formulated to deliver about 0.035 to 3500 mg of tryptanthrin per day. More preferably, an effective daily dose of preferred composition would be formulated to deliver about 0.7 to 700 mg of tryptanthrin per day. Preferably, the effective daily dose is administered once or twice a day.

Preferred embodiments include delivering an effective amount of rosemary or an extract or compound derived from rosemary in combination with other active ingredients. Preferably, a daily dose of preferred compositions would be formulated to deliver about 0.5 to 5,000 mg of rosemary, an extract of rosemary, or rosemary-derived compound per day. More preferably, an effective daily dose of preferred composition would be formulated to deliver about 5 to 2,000 mg of rosemary, an extract of rosemary, or rosemary-derived compound per day. Preferably, the effective daily dose is administered once or twice a day. A certain embodiment provides a composition comprising about 75 mg of rosemary extract or rosemary-derived compound or derivative, to be administered once or twice a day.

Preferred embodiments include delivering an effective amount of a triterpene or diterpene lactone species or derivatives or conjugates thereof in combination with other active ingredients. Preferably, a daily dose of preferred compositions would be formulated to deliver about 0.0005 to 50 mg triterpene or diterpene lactone/kg body weight per day. More preferably, an effective daily dose of preferred compositions would be formulated to deliver about 0.01 to 10 mg triterpene or diterpene lactone/kg body weight per day. Preferably, a daily dose of preferred compositions would be formulated to deliver about 0.035 to 3,500 mg of triterpene or diterpene lactone species per day. More preferably, an effective daily dose of preferred composition would be formulated to deliver about 0.7 to 700 mg of triterpene or diterpene lactone species per day. Preferably, the effective daily dose is administered once or twice a day.

Preferably, an embodiment provides a composition containing an extract of rosemary and a triterpene, such as oleanolic acid, along with an active ingredient, such as a reduced isoalpha acid or tryptanthrin or conjugate thereof. Preferably, an embodiment provides a composition comprising about 0.01 to 500 mg of rosemary extract and about 0.01 to 500 mg of oleanolic acid. Preferably, an embodiment provides a composition capable of producing concentrations in target tissues of 0.1 to 10 µg/g tissue of rosemary extract and about 0.1 to 25 µg/g tissue of oleanolic acid.

A composition of preferred embodiments for topical application would contain about 0.001 to 10 weight percent, preferably about 0.1 to 1 weight percent of a reduced isoalpha acid or derivative or tryptanthrin or conjugate thereof. Preferred embodiments would produce serum concentrations in the ranges of about 0.0001 to 10 µM, preferably about 0.01 to 1 µM of a reduced isoalpha acid or tryptanthrin or conjugate thereof. The preferred embodiments for topical application can further comprise an additional ingredient selected from rosemary, an extract or compound derived from rosemary, a triterpene species or derivatives or conjugates thereof, a diterpene lactone species or derivatives or conjugates thereof, a fraction isolated or derived from hops or tryptanthrin or conjugates thereof, at concentrations of each component of 0.001 to 10 weight percent, preferably 0.1 to 1 weight percent. Preferred embodiments would produce serum concentrations in the ranges of about 0.

Preferred compositions can be administered in the form of a dietary supplement or therapeutic composition. The compositions may be administered orally, topically, transdermally, transmucosally, parenterally, rectally, etc., in appropriate dosage units, as desired.

Preferred compositions for dietary application may include various additives such as other natural components of intermediary metabolism, vitamins and minerals, as well as inert ingredients such as talc and magnesium stearate that are standard excipients in the manufacture of tablets and capsules. For example, one embodiment comprises active ingredients of preferred compositions in combination with glucosamine or chondrotin sulfate.

As used herein, "pharmaceutically acceptable carrier" includes any and all solvents, dispersion media, coatings, isotonic and absorption delaying agents, sweeteners and the like. These pharmaceutically acceptable carriers may be prepared from a wide range of materials including, but not limited to, diluents, binders and adhesives, lubricants, disintegrants, coloring agents, bulking agents, flavoring agents, sweetening agents and miscellaneous materials such as buffers and absorbents that may be needed in order to prepare a particular therapeutic composition. The use of such media and agents for pharmaceutically active substances is well known in the art. Except insofar as any conventional media or agent is incompatible with the active ingredients, its use in preferred compositions is contemplated. In one embodiment, talc, and magnesium stearate are included in the formulation. Other ingredients known to affect the manufacture of this composition as a dietary bar or functional food can include flavorings, sugars, amino-sugars, proteins and/or modified starches, as well as fats and oils.

Dietary supplements, lotions or therapeutic compositions of preferred embodiments can be formulated in any manner known by one of skill in the art. In one embodiment, the composition is formulated into a capsule or tablet using techniques available to one of skill in the art. In capsule or tablet form, the recommended daily dose for an adult human or animal would preferably be contained in one to six capsules or tablets. However, preferred compositions can also be formulated in other convenient forms, such as an injectable solution or suspension, a spray solution or suspension, a lotion, gum, lozenge, food or snack item. Food, snack, gum or lozenge items can include any ingestible ingredient, including sweeteners, flavorings, oils, starches, proteins, fruits or fruit extracts, vegetables or vegetable extracts, grains, animal fats or proteins. Thus, preferred compositions can be formulated into cereals, snack items such as chips, bars, gumdrops, chewable candies or slowly dissolving lozenges. Preferred embodiments contemplate treatment of all types of inflammation-based diseases, both acute and chronic. Preferred formulations reduce the inflammatory response and thereby promotes healing of, or prevents further damage to, the affected tissue. A pharmaceutically acceptable carrier can also be used in the preferred compositions and formulations.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

Example 1

PGE2 Inhibition by RIAA, Selenium, Zinc, and Vitamin D3

This example demonstrates the effect of combinations of reduced isoalpha acids (RIAA), zinc, selenium, and vitamin D3 on prostaglandin E2 (PGE2) release. In this example murine macrophage RAW 264.7 cells were stimulated with LPS for 24 hours in the presence of various combinations RIAA, zinc, selenium, and vitamin D3 and the secretion of PGE2 was determined by enzyme-linked immunosorbent assay methodology.

Methods

Materials—Test compounds were prepared in dimethyl sufoxide (DMSO). RIAA and sodium selenite was supplied by Metagenics (San Clemente, Calif.). Zinc Chloride and Vitamin D3, 1-alpha, 25-dihydroxy were purchased from EMD Biosciences (San Diego, Calif.). Lipopolysaccharide was purchased from Sigma-Aldrich (St. Louis, Mo.).

Cell Culture—Murine macrophage RAW 264.7 cell line was purchased from ATCC (Manassas, Va.) and maintained according to their instructions. Cells treated with either sodium selenite (2 µM) or zinc chloride (169 nM) were grown in serum rich media (10% FBS) in T-75 flasks for two days prior to seeding in 96-well plates. Cells were subcultured in 96-well plates at a density of $1 \times 10^5$ cells per well and allowed to reach 90% confluence. RIAA (20 to 1 µg/ml) and vitamin D3 (355 nM) were added to the cells in serum free media at a final concentration of 0.1% DMSO. Following one hour of incubation with the test compounds, LPS (1 ug/mL) or PBS alone was added to the cell media and incubation continued for an additional 24 hours.

PGE2 Determination—A commercial, non-radioactive procedure for quantification of PGE2 was employed (Cayman Chemical, Ann Arbor, Mich.). The recommended manufacturer procedure was used without modification. Briefly, 50 µl of the medium, along with a serial dilution of PGE2 standard samples, were mixed with appropriate amounts of PGE2-acetylcholinesterase tracer conjugate, and incubated at 4° C. overnight. Fresh Ellman's was prepared and the color development reaction was allowed to progress for 75 minutes at room temperature. The absorbance was measured at 405 nm. The PGE2 concentration was represented as picograms per ml as calculated from the standard curve. The average of four wells was determined for each treatment.

Statistical analysis—Inhibition of PGE2 production was determined by comparison of the PGE2 generated with and without LPS stimulation for 24 hours under the conditions of either a) no test materials added for RIAA and Vitamin D3, b) 2 µM sodium selenite two day preincubation, c) 169 nM zinc chloride two day preincubation, or d) 2 µM sodium selenite and 169 nM zinc chloride two day preincubation. The data was clipped such that values greater than or equal to LPS-stimulated were considered 0% inhibition and values less than or equal to non-stimulated were considered 100% inhibition. The percent inhibition of PGE2 was calculated.

Median Effect Calculations—Median effect calculations were performed using CalcuSyn (Biosoft, Ferguson, Mo.). This program utilizes the Median Effects Model of Chou and Talalay (Adv Enzym Regul (1984) 22:27-55) and fits the equation:

$$\log C = \beta_0 + \beta_1 \log [f_a/(1-f_a)] = \epsilon$$

where $f_a$ is the factional inhibition of the reaction. A minimum of four concentrations were used to determine the dose-response curve and a median inhibitory concentration ($IC_{50}$).

Results

RAW 264.7 cells were stimulated treated for 24 hours with LPS (1 µg/mL) at various concentrations of RIAA, sodium selenite, zinc chloride, or vitamin D3. The medium from the cell culture was recovered and the secreted concentration of PGE2 was determined by ELISA. The percent inhibition of PGE2 was then determined. The values are seen in Table 1 with the average of four wells represented at the PGE2 amount in pg/ml and the standard deviation (SD). FIG. 3 depicts the percent inhibition graphically and the calculated IC50 (µg/ml) values.

Results indicate the following rank of IC50 values for PGE2 inhibition in the RAW 264.7 cell model after 24 hour stimulation: RIAA+VD3 (17.54 µg/ml)>RIAA (9.83 µg/ml)>RIAA+zinc (5.06 µg/ml)>RIAA+selenium+zinc (4.55 µg/ml)>RIAA+selenium (3.23 µg/ml)>RIAA+selenium+VD3 (1.84 µg/ml)>RIAA+zinc+VD3 (1.38 µg/ml)>RIAA+selenium+zinc+VD3 (1.35 µg/ml).

TABLE 1

PGE2 Inhibition by RIAA, Selenium, Zinc, and Vitamin D3

|  | PGE2 (pg/ml) | SD | % Inhib | SD |
| --- | --- | --- | --- | --- |
| Control | 20 | 7 | 100% | 0% |
| LPS | 4038 | 307 | 3% | 3% |

TABLE 1-continued

PGE2 Inhibition by RIAA, Selenium, Zinc, and Vitamin D3

|  | PGE2 (pg/ml) | SD | % Inhib | SD |
|---|---|---|---|---|
| RIAA-20 | 489 | 94 | 88% | 2% |
| RIAA-10 | 2152 | 211 | 47% | 5% |
| RIAA-5 | 3591 | 272 | 11% | 7% |
| RIAA-1 | 4593 | 225 | 0% | 0% |
| D3 + RIAA-20 | 1375 | 339 | 66% | 8% |
| D3 + RIAA-10 | 3119 | 150 | 23% | 4% |
| D3 + RIAA-5 | 3947 | 220 | 7% | 5% |
| D3 + RIAA-1 | 4462 | 510 | 0% | 1% |
| Se Control | 85 | 10 | 100% | 1% |
| Se + LPS | 935 | 152 | 6% | 12% |
| Se + RIAA-20 | 144 | 40 | 93% | 5% |
| Se + RIAA-10 | 294 | 29 | 75% | 3% |
| Se + RIAA-5 | 424 | 72 | 60% | 8% |
| Se + RIAA-1 | 753 | 171 | 21% | 20% |
| D3 + Se + RIAA-20 | 141 | 55 | 94% | 6% |
| D3 + Se + RIAA-10 | 150 | 27 | 92% | 3% |
| D3 + Se + RIAA-5 | 336 | 135 | 70% | 16% |
| D3 + Se + RIAA-1 | 650 | 140 | 34% | 17% |
| Zn Control | 50 | 7 | 99% | 2% |
| Zn + LPS | 317 | 66 | 6% | 11% |
| Zn + RIAA-20 | 79 | 13 | 89% | 5% |
| Zn + RIAA-10 | 125 | 15 | 72% | 6% |
| Zn + RIAA-5 | 199 | 52 | 44% | 19% |
| Zn + RIAA-1 | 318 | 75 | 10% | 8% |
| Zn + D3 + RIAA-20 | 62 | 23 | 94% | 7% |
| Zn + D3 + RIAA-10 | 100 | 22 | 81% | 8% |
| Zn + D3 + RIAA-5 | 163 | 10 | 70% | 4% |
| Zn + D3 + RIAA-1 | 188 | 84 | 48% | 31% |
| Zn + Se Control | 44 | 3 | 100% | 1% |
| Zn + Se + LPS | 312 | 48 | 7% | 9% |
| Zn + Se + RIAA-20 | 70 | 9 | 90% | 3% |
| Zn + Se + RIAA-10 | 136 | 15 | 61% | 9% |
| Zn + Se + RIAA-5 | 170 | 27 | 53% | 10% |
| Zn + Se + RIAA-1 | 292 | 83 | 15% | 19% |
| D3 + Zn + Se + RIAA-2 | 51 | 6 | 97% | 2% |
| D3 + Zn + Se + RIAA-1 | 75 | 22 | 88% | 8% |
| D3 + Zn + Se + RIAA-5 | 123 | 9 | 70% | 3% |
| D3 + Zn + Se + RIAA-1 | 178 | 30 | 50% | 11% |

Example 2

The Effect of RIAA, Vitamin D3, Zinc, and Selenium on Symptomology of Patients with Crohn's Disease The purpose of this example is to demonstrate the effects of a RIAA, vitamin D3, zinc, and selenium composition (hereinafter "Kaprex AI") on disease associated symptomolgy in patients with Crohn's disease.

Patient A (Case Abstract #096CD1105)

Patient's Presentation and History

A 61 year-old female presented for management of Crohn's disease (CD). Her GI issues started while in college and she underwent partial colectomy. CD was diagnosed a few years later. Repeat colectomy was subsequently required until eventually a total of ⅔ of her colon and ½ of her small bowel had been excised. Patient was currently quite symptomatic, with abdominal distention and crampy abdominal pain often involving her entire abdomen, before and after BM's. Pain was managed with oxycodone. Diarrhea occurred 3-6 times/day. She complained of fatigue, mild nausea, and noted thigh muscle weakness which she related to high dose prednisone.

Patient, at study initiation, was on the following prescription medications: Forteo™ (teriparatide) 20 mcg subcut. qd; Dirsdol® (ergocalciferol, vit $D_2$), 50,000 IU q month; Oxycontin® (oxycodone HCl), 50 mg tid; prednisone, 40 mg qd; Cymbalta® (duloxetine HCl), 60 mg qd; Nexium® (esomeprazole), 40 mg bid; furosemide, 40 mg bid; KCl 10 mEq, 3 capsules qd; Vagifem® (estradiol), 1 tablet twice/week; propanolol, 20 mg bid; Lorazepam, 0.5 mg bid prn; oxicodone-5 mg, 2 tablets prn; Phenergan® (promethazine), 25 mg prn; Ambien® (zolpidem) 5 mg, at bedtime prn; Flexeril® (cyclobenzaprine HCl), 10 mg every 4-6 h prn; cortisone injections for bursitis in hips prn; Benadryl® (dyphenhydramine HCl), 25 mg prn; Allegra® (fexofenadine HCl) 180 mg/day prn.

She was on the following non-prescription medications and supplements: calcium carbonate, 600 mg bid; multivitamin w/iron, 1 qd; vitamin B complex, 1 qd; vitamin $B_{12}$, 1000 mg IM q 2 weeks; EPA-DHA 720, 2 capsules/day; ferrous gluconate, 324 mg qd; vitamin C, 500 mg qd; aspirin, 81 mg qd; Maalox® (Al and Mg hydroxides), prn.

Treatment Plan

The patient was instructed to begin inflammatory-modulating medical food with added reduced iso-alpha-acids from hops (RIAA) and Vitamin D, working up to 2 scoops twice a day.

3-5-Week Results

At the 3-week visit, patient noted that her BMs had decreased from up to 10/day to only one/day. She continued to be tired all the time and had lots of lower extremity swelling. Patient was instructed to discontinue the current medical food and to begin UltraInflamX® medical food, 2 scoops bid, a supplement containing 200 mg RIAA, 1 tablet bid along with the medical food, and another containing 2000 IU Vit D (Iso D3), 1 tablet qd. She was also started on LactoViden, 1 capsule bid. After 5 weeks, patient reported lots of sweating, especially after exertion, and at night. Patient was instructed to discontinue the vitamin D and RIAA supplements and begin supplement combination RIAA (225 mg), vitamin D (500 IU), zinc (5 mg) and Selenium (50 mcg), 1 tablet bid (Kaprex AI). She was told to continue on the UltraInflamX® medical food, 2 scoops bid, and LactoViden, 1 capsule bid, and to add EstroFactors, 3 tablets qd. She was also asked to discontinue the EPA/DHA 720 and to begin EPA-DHA ES (enteric coated), 2 capsules tid. Patient was started on an elimination diet.

7-12-Week Results

At the 7-week visit, the patient noted consistent formed stools but no further improvement. A stool test was positive for gluten sensitivity. Kaprex AI was increased to 1 in the AM and 2 with dinner and she was told to discontinue oats. After 9 weeks, Patient noted a real difference in energy. Her head felt clearer and she felt more active. BMs had continued to be good, normally from 0-1/day. The patient was instructed to continue on the prescribed protocol, but to increase the dose of combination supplement to to 2 tablets bid. She was also started on DHEA spray (BioSom) 1 spray bid. After 12 weeks, patient felt 50-75% improved from start of protocol. Abdominal distetion had resolved; pain was much better overall; she was using less breakthrough pain medication. She was unable to tolerate BioSom due to gastric reflux. Fatigue persisted.

Results (Table 2)

This case shows the developing benefits of addition of a protocol combining an inflammatory-modulating medical food, RIAA, vitamin D, Zn, and Se, and diet to standard

TABLE 2

Summary MSQ*, MOS† and SIBDQ Questionnaire Scores

|  | Aug. 25, 2005 | Sep. 13, 2005 | Sep. 27, 2005 | Oct. 10, 2005 | Oct. 21, 2005 | Nov. 10, 2005 |
|---|---|---|---|---|---|---|
| MSQ* | 73 | 53 | 37 | 39 | 42 | 21 |
| MOS-PCS† | 14.9 | — | 23.2 | 17 | 17 | 27.3 |
| MOS-MCS† | 54.2 | — | 43.9 | 48 | 57.6 | 45.7 |

Patient B (Case Abstract #092CD1105)

Patient's Presentation and History

A 57 year-old female presented with a previous diagnosis of Crohn's disease. She had been diagnosed with anemia 8 years earlier and with Crohn's disease 2 years later, after colonoscopy revealed ulcers in terminal ileum. She was placed on sulfasalazine, but later discontinued it due to stomach cramping. After return of symptoms and worsening of anemia 2 years later, repeat colonoscopy revealed new ulcerations in ileum. Patient was started on mesalamine with improvement of symptoms, and budesonide was added later. She felt better but stool frequency was never less than 2-3 times/day. Four months before presentation, patient began a high fiber diet and she promptly became very sick with vomiting, diarrhea, and blood in stool. She was hospitalized, given IV steroids and antibiotics, and was started on azathioprine, and a 3-month course of budesonide.

Patient was currently on the following prescription medications: Mesalamine 1600 mg tid and azathioprine 100 mg qd for Crohn's; venlafaxine HCl, 112.5 mg qd for hot flashes; alendronate, 70 mg weekly for osteopenia; atorvastatin, 10 mg qd for hypercholesterol-emia; propoxyphene+acetaminophen combination drug for joint pain, as needed; Patient took ASA daily for 30 years. She was on the following non-prescription medications and supplements: ibuprofen or aspirin prn; multivitamin, 1 tablet qd; Calcium citrate 630 mg+400 Vit D bid; lactase enzyme.

Treatment Plan

The patient was instructed to stop all current supplements and to begin inflammatory-modulating medical food with added reduced iso-alpha-acids from hops (RIAA) and Vitamin D, working up to 2 scoops twice a day.

3- through 7-Week Results

At the 3-week visit, patient reported that immediately after starting the medical food she started having normal BMs—formed, large caliber stools, 1-2 BMs/day. Stools then became softer and more frequent and she was currently having 4-5 soft BM's per day with a little gas and no discomfort. Her sleeping was disturbed by hot flashes. A combination isoflavone supplement, (EstroFactors) 3 tablets with lunch, was added for hot flashes. A stool test for gluten sensitivity was positive and she was started on a gluten free diet. After 5 weeks, patient's BMs had normalized. Patient was asked to discontinue the current formulation of medical food and begin UltraInflamX® medical food 2 scoops bid, along with a supplement containing 200 mg RIAA, 1 tablet bid, and another containing 2000 IU Vit D (Iso D3), 1 tablet qd. She was also placed on an elimination diet. By the 7-week visit her hot flashes had improved from previously 20/day and strong to current 10-14/day and milder. Patient rated her overall improvement at 25% from the start of the program. Patient was asked to continue on prescribed doses of UltraInflamX medical food and combination isoflavone, and to begin supplement combination RIAA (225 mg), vitamin D (500 IU), zinc (5 mg) and Selenium (50 mcg), 1 tablet bid (Kaprex AI) along with the medical food. She was also started on combination EPA-DHA (600 mg+400 mg) and Vitamin E (20 IU), 2 softgels tid, Dairy-free probiotic supplement (*Lactobacillus acidophilus* NCFM strain, *Bifidobacterium lactis*) (UltraFlora IB), 1 capsule bid, and hematinic formula supplement (highly absorbable iron, vitamins $B_6$ and $B_{12}$, thiamin, folate, succinic acid, glycine) (Hemagenics), 1 tablet bid, for anemia.

9- through 16-Week Results

Patient was seen again 9- and 13-weeks after starting the protocol. At both visits she reported feeling well, with normalized BMs, and less intense hot flashes. She had continued elimination diet and food reintroduction. At the 16-week visit, patient commented that she was having 1 formed BM/day, no diarrhea or other abnormalities. She reported an excellent level of energy, and no joint pain. Laboratory results indicated normalization of fecal calprotectin and Eosinophil Protein X, IgM *Candida* and IgG *E. coli*. Patient was instructed to continue on prescribed plan.

Results (Table 3)

This case shows the positive effect that a protocol combining an inflammatory-modulating medical food, RIAA, vitamin D, Zn, and Se, and diet, had on a patient presenting with a history of Crohns' disease and several other symptoms relating to immune-inflammatory conditions.

TABLE 3

Summary MSQ*, MOS† and SIBDQ Questionnaire Scores

|  | Initial Visit | 3 weeks | 5 weeks | 7 weeks | 9 weeks | 16 weeks |
|---|---|---|---|---|---|---|
| MSQ* | 39 | 36 |  | 34 | 21 | 10 |
| MOS-PCS† | — | 44.4 | — | — | 50.9 | 51.3 |
| MOS-MCS† | — | 47.9 | — | — | 51.8 | 57.3 |
| SIBDQ‡ |  |  |  |  |  |  |
| Total | 4.2 | — | 4.1 | 5.3 | 6.1 | 6.5 |
| Bowel | 4.0 | — | 4.0 | 4.3 | 5.6 | 6.3 |
| Emotional | 4.0 | — | 4.3 | 6.0 | 6.3 | 6.3 |
| Systemic | 6.0 | — | 3.0 | 5.5 | 6.0 | 6.5 |
| Social | 3.0 | — | 5.0 | 5.5 | 6.5 | 7 |

*The MSQ is a clinical tool for the evaluation of general physical symptoms. Total scores above 75 are generally associated with substantial symptomatology and disability; scores below 30 generally indicate few or low intensity symptoms
†The MOS SF-36 is a well-validated general quality of life questionnaire that summarizes health outcome in two reliable reproducible scores: the Physical Component Summary (PCS) and the Mental Component Summary (MCS). On a scale of 0-100, 50 is the mean for the US. Higher scores are associated with healthier individuals.
‡The SIBDQ is a shortened version of the Inflammatory Bowel Disease Questionnaire (IBDQ), which has been valuable in assessing important clinical changes in the health and outcomes of patients with IBD. The 10 items in the SIBDQ provide information in four categorical scores: bowel, systemic, social, and emotional. A higher score indicates a better quality of life, while a lower score indicates a poorer quality of life.

Example 3

The Effect of RIAA, Vitamin D3, Zinc, and Selenium on Symptomology of Patients with Rehumatoid Arthritis The purpose of this example is to demonstrate the effects of a RIAA, vitamin D3, zinc, and selenium composition on disease associated symptomolgy in patients with rheumatoid arthritis.

Patient A (Case Abstract # 090RA1105)

Patient's Presentation and History

A 51-year-old female presented with a previous diagnosis of rheumatoid arthritis (RA). She complained of swollen knees, muscle aching, and intermittent nausea and fatigue. She also noted that her hands and bottom of her feet would get hot.

Assessment and Plan

RA with negative rheumatoid factor. Obesity. Iron deficiency. The patient was instructed to begin inflammatory-modulating medical food with added reduced iso-alpha-acids from hops (RIAA) and Vitamin D, working up to 2 scoops bid. (UltraInflamX AI).

5- through 7-Week Results

At the 5-week visit, patient reported that she was feeling better and she noted more energy. She was walking again without problem and was able to go up and down stairs more easily. Patient was started on a 21-day elimination diet followed by careful food reintroduction. After 7 weeks, the patient rated her joint pain at a level of 2-3 (scale of 1-10), down from 6-7 before beginning the protocol. She was able to go up and down the stairs facing forward, while previously she had to go down sideways. Elbows, knees, and hands only bothered her occasionally; her mind was clear and she felt well. Patient was asked to discontinue the current formulation of medical food and begin UltraInflamX® medical food, 2 scoops bid, along with a supplement containing 200 mg RIAA, 1 tablet bid, and another containing 2000 IU Vit D (Iso D3), 1 tablet qd.

9- through 13-Week Results

Nine weeks into the program, patient was very compliant and reported feeling much improvement in her arthritic pain symptoms. She noted no nausea or fatigue. Her feet had not felt hot in 2 weeks. Muscle aching has also resolved. Patient had been on the elimination diet for 4 weeks, and reported to be 100% compliant. She was instructed to discontinue the RIAA and vitamin D supplements and to begin a supplement combination RIAA (225 mg), vitamin D (500 IU), zinc (5 mg) and Selenium (50 mcg), 1 tablet bid. (Kaprex AI). At the 13-week visit, the improvement had been sustained. Patient was much more active, felt very energetic, and was no longer tired. She noted that her only limitation was heavy lifting, and she reported that she had not taken naproxen in the previous 5-6 weeks.

Patient was instructed to increase the dose of the combination supplement to 2 tablets bid, to continue on UltraInflamX medical food, 2 scoops bid, and to begin a combination EPA-DHA (600 mg+400 mg) and Vitamin E (20 IU), 2 softgels tid.

Results (Tables 4 & 5)

This case shows the positive effect that a protocol combining an inflammatory-modulating medical food, RIAA, vitamin D, Zn and Se and diet had on a patient presenting with rheumatoid arthritis and other inflammation-related symptoms.

TABLE 4

Summary MSQ* and MOS[†] questionnaire scores

|  | Initial Visit | 3 weeks | 5 weeks | 7 weeks | 9 weeks | 13 weeks |
|---|---|---|---|---|---|---|
| MSQ* | 21 | 29 | 24 | 5 | 4 | 8 |
| MOS-PCS[†] | — | 38.7 | 49.3 | — | 51.0 | 50.0 |
| MOS-MCS[†] | — | 55.6 | 55.7 | — | 61.7 | 61.7 |

*The MSQ is a clinical tool for the evaluation of general physical symptoms. Total scores above 75 are generally associated with substantial symptomatology and disability; scores below 30 generally indicate few or low intensity symptoms.
[†]The MOS SF-36 is a well-validated general quality of life questionnaire that summarizes health outcome in two reliable reproducible scores: the Physical Component Summary (PCS) and the Mental Component Summary (MCS). On a scale of 0-100, 50 is the mean for the US. Higher scores are associated with healthier individuals.

TABLE 5

AIMS2-A[‡] Questionnaire Scores

| Health Status Components | Possible score range | 3 weeks | 9 weeks | 13 weeks |
|---|---|---|---|---|
| Physical | 0-10 | 1.2 | 0.25 | 0.33 |
| Symptoms | 0-10 | 5.5 | 2 | 0.5 |
| Social Interaction | 0-10 | 3.3 | — | 2.8 |
| Role | 0-10 | — | 0 | — |

[‡]The AIMS2-Abridged questionnaire is a clinical tool for the evaluation of health status and outcomes of individuals with rheumatic diseases. A low score value indicates a high health status, while a high score value indicates poor health.

Patient B (Case Abstract # 091RA1105)

Patient's Presentation and History

A 52-year-old female presented in September 2005 with a previous diagnosis of rheumatoid arthritis (RA). About 3 years before presentation, she was switched to Enbrel® (etanercept), 25 mg twice weekly. Although she did better on his medication, foot, hand and wrist pain persisted. She was still getting tired, and her hands and feet would swell off and on. About 5-6 weeks prior to presentation, she had surgery on her left foot for removal of pins that stabilized her ankle, placed 2-3 years earlier.

Assessment and Plan

RA with high RF. Fatigue, secondary to RA. Hypothyroidism. Gluten sensitivity. Low normal vitamin D. The patient was instructed to begin UltraInflamX® medical food working up to 2 scoops twice a day. She was also placed on a supplement containing 200 mg RIAA, 1 tablet bid.

2-Week Results

At the 2-week visit, the patient reported that her joint pain had not lessened. She noted no change in fatigue symptoms. Additionally, she had been having mild hot flashes during the day and night. The patient was instructed to continue UltraInflamX, to discontinue RIAA, and to begin a supplement combination RIAA (225 mg), vitamin D (500 IU), zinc (5 mg) and Selenium (50 mcg), (Kaprex AI) 1 tablet bid. Additionally, she was instructed to discontinue her fish oil concentrate, to start a supplement combination EPA-DHA (600 mg+400 mg) and Vitamin E (20 IU) (EPA-DHA ES), 2 softgels tid, to begin a combination isoflavone supplement (EstroFactors), 3 tablets daily, and to begin a gluten-free diet.

4-Week Results

After 4 weeks, patient was feeling better, with less fatigue, but joint swelling had not improved and she was constipated. Her hot flashes had definitely lessened. Stool analysis indicated lack of intestinal bifidobacteria; Women's Hormonal Health Assessment indicated depressed DHEA-S, 2(OH) estrone, and 2/16 (OH) estrogen ratio, as well as elevated estriol. The patient was advised to continue with the UltraInflamX medical food, RIAA/VitD/Zn/Se combination supplement, fish oil supplement. She was instructed to take the 3 tablets of isoflavone supplement with dinner. She was started on I3C (Meta I3C), 1 tablet bid, and a liquid DHEA spray, bid. (Bio Som) She was advised to add 1 tsp. flax seeds to her UltraInflamX for constipation.

6-Week Results

Patient reported a substantial improvement in joint pain after 5 weeks of starting the protocol. Pain was gone in her knees, and she noted only mild discomfort in hands when using them a lot, i.e. working in the yard. She also noted that her hands were more sore if she ate wheat. Her fatigue symptoms were better, although not totally gone, and she had increased energy. Hot flashes were mild and no longer woke her up. Sedimentation rate had normalized, but Rheumatoid Factor remained very elevated. The patient was advised to continue on UltraInflamX medical food 2 scoops bid, RIAA/VitD/Zn/Se combination supplement 1 bid, combination isoflavone supplement 3 tablets with lunch, fish oil d 2 softgels tid, I3C 1 bid, DHEA spray, 1 squirt bid.

Results (Table 6 & 7)

This case shows the positive effect that a protocol combining an inflammatory-modulating medical food, RIAA, vitamin D, Zn and Se and diet had on a patient presenting with several symptoms relating to immune-inflammatory conditions.

TABLE 6

Summary MSQ* and MOS† questionnaire scores

|  | Initial visit | 2 weeks | 4 weeks | 6 weeks |
|---|---|---|---|---|
| MSQ* | 14 | 8 | 7 | 5 |

*The MSQ is a clinical tool for the evaluation of general physical symptoms. Total scores above 75 are generally associated with substantial symptomatology and disability; scores below 30 generally indicate few or low intensity symptoms

TABLE 6

Laboratory Values

|  | Reference Range/units | Initial Visit | 6 weeks |
|---|---|---|---|
| Sedimentation Rate | 0-30 mm/hr | 57 | 27 |

Patient C (Case Abstract # 093RA1105)

Patient's Presentation and History

A 51 year-old female presented with a chief complaint of arthritic pain of 3 years duration. She currently suffered from moderate leg cramps; foot cramps; joint pain, deformity, redness and stiffness; muscle aches, pains and weakness, and mild muscle spasms, all of which responded partially to ibuprofen and some supplements. Rheumatoid arthritis (RA) was diagnosed in June of 2003, and she was placed on a blood-type diet and supplements. She noted about a 50% improvement with this protocol, but eventually she discontinued it and her health worsened again.

Assessment and Plan

The patient was instructed to begin inflammatory-modulating medical food with added reduced iso-alpha-acids from hops (RIAA) and Vitamin D, working up to 2 scoops bid. (UltraInflamX AI). She was also placed on an elimination diet to be started 2 weeks later.

4- through 7-Week Results

At the 4-week visit, the patient reported that she was doing much better. She was not as tired as before and she had less pain, with no further back flare-ups. She had been compliant on the elimination diet and had lost 3 lb. Stool analysis done 2 weeks earlier indicated slight dysbiosis. Patient was asked to continue with the prescribed medical food and to begin the following: RIAA, 200 mg tablet, 1 tablet bid; supplement containing 2000 IU Vitamin $D_3$ with isoflavones (IsoD3), 1 tablet qd; supplement combination EPA-DHA (600 mg+400 mg) and Vitamin E (20 IU) (EPA-DAH ES), 2 softgels bid. At the 7-week visit patient related her discovery of intolerance to wheat—as a result of the food re-introduction protocol—which produced fatigue and exacerbation of pain in her hands. The RIAA and vitamin D supplements were replaced by a supplement combination RIAA (225 mg), vitamin D (500 IU), zinc (5 mg) and Selenium (50 mcg), (Kaprex AI) 1 tablet bid along with the medical food.

9-Week Results

Nine weeks into the program, the patient's pain symptom improvement had sustained and she continued to challenge foods. She felt quite energetic and was very happy with her progress. Additionally, her blood pressure had normalized to 120/84, from initial 151/95. She was instructed to continue the food re-introduction, and the prescribed doses of medical food, combination supplement, and fish oil supplement. Two dairy-free probiotic supplements (LactoViden and BifoViden) to be taken 1 capsule of each upon rising and before bedtime, were added to improve her gut microbiological balance. She was also placed on a supplement combination Vit $B_{12}$, folic acid and intrinsic factor, 1 tablet in the morning.

Results

This case shows the positive effect that a protocol combining an inflammatory-modulating medical food, RIAA, vitamin D, Zn and Se and diet had on a patient presenting with several symptoms relating to immune-inflammatory conditions.

TABLE 8

Summary MSQ* and MOS† questionnaire scores

|  | Initial | 2 weeks | 4 weeks | 7 weeks | 9 weeks |
|---|---|---|---|---|---|
| MSQ* | 43 | 49 | 26 | 6 | 22 |
| MOS-PCS† | 26.5 | 26.4 | — | 36.1 | — |
| MOS-MCS† | 27.4 | 33.7 | — | 57.9 | — |

*The MSQ is a clinical tool for the evaluation of general physical symptoms. Total scores above 75 are generally associated with substantial symptomatology and disability; scores below 30 generally indicate few or low intensity symptoms.
†The MOS SF-36 is a well-validated general quality of life questionnaire that summarizes health outcome in two reliable reproducible scores: the Physical Component Summary (PCS) and the Mental Component Summary (MCS). On a scale of 0-100, 50 is the mean for the US. Higher scores are associated with healthier individuals.

TABLE 9

AIMS2-A‡ Questionnaire Scores

| Health Status Components | Possible score range | Initial | 2 weeks | 4 weeks | 7 weeks | 9 weeks |
|---|---|---|---|---|---|---|
| Physical | 0-10 | 2.9 | — | — | 1.18 | 1.9 |
| Symptoms | 0-10 | 9 | — | — | 4.5 | 4.5 |
| Social Interaction | 0-10 | 5.5 | — | — | 4.8 | 4.3 |
| Role | 0-10 | 5.6 | — | — | 5 | 5.6 |

‡The AIMS2-Abridged questionnaire is a clinical tool for the evaluation of health status and outcomes of individuals with rheumatic diseases. A low score value indicates a high health status, while a high score value indicates poor health.

Example 4

The Effect of RIAA, Vitamin D3, Zinc, and Selenium on Symptomology of Patients with Raynaud's Phenomenon The purpose of this example is to demonstrate the effects of a RIAA, vitamin D3, zinc, and selenium composition on disease associated symptomolgy in patients with Raynaud's phenomenon.

Patient A (Case Abstract #094RD1105)

Patient's Presentation and History

A 54-year-old white female presented in with a long-term history of Raynaud's in her hands and fingers.

Assessment and Plan

The patient was instructed to begin inflammatory-modulating medical food with added reduced iso-alpha-acids from hops (RIAA) and Vitamin D, working up to 2 scoops bid. (UltraInflamX AI)

2- through 4-Week Results

At the 2-week visit, the patient reported no change in symptoms and she was placed on an elimination diet to assess potential food intolerances. Based on laboratory results that indicated depressed 2/16 alpha-hydroxyestrone ratio, patient was started on a supplement containing 150 mg indole-3-carbinol (I3C), 1 tablet bid with meals. (Meta I3C). After 4 weeks, the patient reported that her fingertips were less reactive to cold, and she noted significant improvement in her knee arthritis symptoms. She was advised to discontinue the medical food with added reduced RIAA and Vitamin D, and to begin UltraInflamX® medical food, 2 scoops, twice a day. A tablet containing 200 mg RIAA was added, to be taken twice a day along with the medical food servings. She was also instructed to begin a supplement containing 2000 IU Vitamin $D_3$ with isoflavones (IsoD$_3$), 1 caplet per day. Based on stool analysis that indicated lack of bifidobacteria, she was also placed on 2 probiotic supplements (BifoViden and LactoViden) providing a proprietary blend of live organisms, 1 capsule bid each (upon rising and at dinner).

6- through 8-Week Results

At the 6-week visit, patient related that her hands seemed to be warm even though cooler Fall weather had started, and that the level of discomfort in her fingers was much less than before starting the protocol. Patient was instructed to continue on UltraInflamX medical food, 2 scoops bid, probiotics, and I3C, to discontinue the RIAA and Vit D3 supplements, and to start a supplement combination RIAA (225 mg), vitamin D (500 IU), zinc (5 mg) and Selenium (50 mcg), (Kaprex AI) 1 tablet bid.

After 8 weeks, patient continued to report improved Raynaud's and arthritic symptoms and she was instructed to remain on the prescribed protocol.

Results (Table 10)

In this case, changes in subjective assessment suggest that a protocol combining an inflammatory-modulating medical food, RIAA, vitamin D, Zn and Se may be beneficial as nutritional support for patients with immune-inflammatory conditions such as Raynaud's.

TABLE 10

Questionnaire's scores

| Date | Initial visit | 2 weeks | 4 weeks | 6 weeks |
|---|---|---|---|---|
| MSQ* | 33 | 8 | 16 | 18 |

Patient B (Case Abstract #095EM1105)

Patient's Presentation and History

A 44 year old Caucasian female presented with a history of erythromelalgia with hot painful feet, and Raynaud's phenomenon with cold and painful fingers.

Assessment and Plan

Erythromelalgia. Raynaud's phenomenon. Dysbiosis. Fatigue probably from sleep apnea and restless leg syndrome. Asthma and migraine headaches possibly exacerbated by food allergies. The patient was instructed to begin inflammatory-modulating medical food with added reduced iso-alpha-acids from hops (RIAA) and Vitamin D, working up to 2 scoops bid. (UltraInflamX AI)

2- through 5-Week Results

At the 2-week visit, patient reported 50% improvement of symptoms and less fatigue. The pain in her shoulder had decreased. She was instructed to discontinue the prescribed medical food and to begin Ultra-InflamX®, 2 scoops bid, RIAA 200 mg, 1 tablet bid; a supplement containing 2000 IU Vitamin $D_3$ with isoflavones (IsoD3), 1 tablet qd; a supplement combination EPA-DHA (600 mg+400 mg) and Vitamin E (20 IU) (EPA-DHA ES), 2 softgels bid; and a supplement combination vitamin $B_{12}$, folic acid and intrinsic factor (Intrinsi $B_{12}$/Folate), 1 tablet qd. Patient was also started on an elimination diet. After 5 weeks, the patient reported a 100% reduction in hand pain, and noted less swelling and redness in her feet. She had had no migraines and very few headaches, higher energy levels, improved sleep, and resolved intestinal gas. Laboratory results indicated positive endomysial antibodies, positive Antigliadin antibodies and positive transglutaminase antibodies, elevated Eosinophil Protein X and calprotectin, and no intestinal growth of beneficial lactobacillus and bifidobacterium. She was instructed to continue on the prescribed nutraceuticals, except for switching from RIAA 200 mg to a supplement combination RIAA (225 mg), vitamin D (500 IU), zinc (5 mg) and Selenium (50 mcg), 1 tablet bid. (Kaprex AI) Additionally, she was placed on 2 probiotic supplements providing a proprietary blend of live organisms, 1 capsule bid each (upon rising and at dinner), (BifoViden and LactoViden) and was instructed to add 1 teaspoon of a combination glutamine, deglycyrrhinized licorice root (DGL), and aloe extract (3500 mg/500 mg/50 mg) to her medical food shakes. (Glutagenics) Patient was started on a gluten-free diet.

8- and 12-Week Results

After 8 weeks, patient felt she no longer needed to take citalopram for depression, and pramipexole for sleeping, so she discontinued both. She had decreased gabapentin dose from 9 to 3 tablets per day with no increase in pain. Physical exam revealed fairly normal looking hands with only slight erythema and feet slightly cool to the touch, but without erythema. Patient was instructed to continue on the prescribed program. At the 12-week visit, patient reported that she could actually stand on her feet without any pain at all. She had stopped all medications and had no pain. She was still having some Raynaud's symptoms. Laboratory tests indicated normalized homocysteine, improved intestinal permeability, and improved gut immunology markers. Fecal mycology was positive for Candida albicans. She was instructed to continue on medical food, fish oils, probiotics, and DGUaloe, to increase RIAA/vitD/Zn/Se supplement to 1 tablet tid, restart vit D/isoflavones supplement at 1 tablet qam, and to begin herbal formula containing berberine for intestinal dysbiosis, 2 tablet bid. (Candibactin-BR)

Results (Table 11)

Changes in subjective assessment suggest that a protocol combining an inflammatory-modulating medical food, RIAA, vitamin D, Zn, and Se and diet may be beneficial for improvement of erythromelalgia and Raynaud's.

TABLE 11

| | Questionnaire's scores | | | | |
| | Date | | | | |
| | Initial visit | 2 weeks | 5 weeks | 8 weeks | 12 weeks |
|---|---|---|---|---|---|
| MSQ* | 24 | 27 | 7 | 12 | 5 |
| MOS-PCS† | 16.6 | 16.2 | — | — | 48.5 |
| MOS-MCS† | 53.7 | 54.5 | — | — | 58.4 |

*The MSQ is a clinical tool for the evaluation of general physical symptoms. Total scores above 75 are generally associated with substantial symptomatology and disability; scores below 30 generally indicate few or low intensity symptoms
†The MOS SF-36 is a well-validated general quality of life questionnaire that summarizes health outcome in two reliable reproducible scores: the Physical Component Summary (PCS) and the Mental Component Summary (MCS). On a scale of 0-100, 50 is the mean for the US. Higher scores are associated with healthier individuals.

Example 5

The Effect of RIAA, Vitamin D3, Zinc, and Selenium on Symptomology of a Patient with Systemic Lupus erythematosus The purpose of this example is to demonstrate the effects of a RIAA, vitamin D3, zinc, and selenium composition on disease associated symptomolgy in patients with systemic lupus erythematosus.

Patient A (Case Abstract #098SLE1105)

A 40 year-old female presented with a previous diagnosis of SLE and Raynaud's phenomenon.

Treatment Plan

The patient was instructed to begin UltraInflamX® medical food, 2 scoops bid, along with 2 neutraceuticals: 200 mg RIAA, 1 tablet bid, and 2000 IU Vit D, 1 tablet qd. (Iso D3)

3- through 5-Week Results

At the 3-week visit, patient was doing well and had more energy. Her intestinal tract was improving and she had no bloating, nor other problems. Her muscles were a little more sore and she was getting muscle spasms, especially at night. The patient was instructed to continue on the medical food 2 scoops bid, to discontinue RIAA 200 mg and vitamin D supplement and to begin supplement combination RIAA (225 mg), vitamin D (500 IU), zinc (5 mg) and selenium (50 mcg), 1 tablet bid. (Kaprex AI) She was also started on a combination EPA-DHA (600 mg+400 mg) and Vitamin E (20 IU), 2 softgels tid, and instructed on beginning an elimination diet.

After 5 weeks, her muscles felt better and she was less stiff and less sore. Her Raynaud's phenomenon had not changed much, and she rated her discomfort at 3 on a scale of 1-10, with occasional flairs to 9. The patient was placed onMag-Glycinate, 1 tablet upon rising and going to bed, a dairy-free probiotic supplement, 1 capsule upon rising and going to bed, (BifoViden) and Indole-3-carbinol 150 mg, 1 tablet tid (Meta I3C) were added to the protocol. Patient was also counseled on gradual reintroduction of foods into her diet.

7- through 9-Week Results

After 7-weeks, patient continued to feel better, noting 50% reduction in joint pain and 50% improvement in energy since starting the program. She stated that her Raynaud's seemed unchanged, with episodes occurring about once/day. She continued to challenge foods, with no adverse responses.

Nine weeks after starting the program, patient reported that, overall, she felt good. She no longer had pain in muscles and joints, and her hips no longer ached while on the treadmill. Her level of energy continued to improve also. IBS symptoms were resolved and her GI tract felt great. There had been no improvement on Raynaud's.

Laboratory tests indicated continued positive ANA screen, titer 1:320. A supplement containing 2000 IU Vitamin $D_3$ with isoflavones, 1 tablet in the morning, (IsoD3) was added to her protocol in view of repeat suboptimal 25(OH) vit D level. Patient was to be followed up on a monthly basis.

Results (Table 12)

This case shows the positive effect that a protocol combining an inflammatory-modulating medical food, RIAA, vitamin D, Zn, and Se, and diet, had on a patient presenting with a history of SLE and related GI symptoms.

TABLE 12

| | Summary MSQ*, MOS† | | | |
| | Initial Visit | 3 weeks | 5 weeks | 9 weeks |
|---|---|---|---|---|
| MSQ* | 23 | 15 | 15 | 19 |
| MOS-PCS† | 33.7 | 36.7 | 43.9 | 52.3 |
| MOS-MCS† | 58.3 | 61.9 | 56.4 | 56.3 |

*The MSQ is a clinical tool for the evaluation of general physical symptoms. Total scores above 75 are generally associated with substantial symptomatology and disability; scores below 30 generally indicate few or low intensity symptoms
†The MOS SF-36 is a well-validated general quality of life questionnaire that summarizes health outcome in two reliable reproducible scores: the Physical Component Summary (PCS) and the Mental Component Summary (MCS). On a scale of 0-100, 50 is the mean for the US. Higher scores are associated with healthier individuals.

Example 6

Inhibition of PGE$_2$ synthesis in Stimulated and Nonstimulated Murine Macrophages by Hops (*Humulus lupulus*) Compounds and Derviatives Summary—This example illustrates the potency of hops fractions and derivatives to inhibit COX-2 synthesis of PGE$_2$ preferentially over COX-1 synthesis of PGE$_2$ in the murine macrophage model.

Chemicals and reagents—Bacterial lipopolysaccharide (LPS; B *E. coli* 055:B5) was from Sigma (St. Louis, Mo.). Hops fractions (1) alpha hop (1% alpha acids; AA), (2) aromahop OE (10% beta acids and 2% isomerized alpha acids, (3) isohop (isomerized alpha acids; IAA), (4) beta acid solution (beta acids BA), (5) hexahop gold (hexahydro isomerized alpha acids; HHIAA), (6) redihop (reduced isomerized-alpha acids; RIAA), (7) tetrahop (tetrahydro-iso-alpha acids THIAA) and (8) spent hops were obtained from Betatech Hops Products (Washington, D.C., U.S.A.). The spent hops were extracted two times with equal volumes of absolute ethanol. The ethanol was removed by heating at 40° C. until a only thick brown residue remained. This residue was dissolved in DMSO for testing in RAW 264.7 cells. Unless otherwise noted, all standard reagents were obtained from Sigma (St. Louis, Mo.) and were the purest commercially available.

Cell culture—RAW 264.7 cells, obtained from American Type Culture Collection (Catalog #TIB-71, Manassas, Va.), were grown in Dulbecco's Modification of Eagle's Medium (DMEM, Mediatech, Herndon, Va.) and maintained in log phase. The DMEM growth medium was made by adding 50 mL of heat inactivated FBS and 5 mL of penicillin/streptomycin to a 500 mL bottle of DMEM and storing at 4° C. The growth medium was warmed to 37° C. in water bath before use.

On day one of the experiment, the log phase RAW 264.7 cells were plated at $8 \times 10^4$ cells per well in 0.2 mL growth medium per well in a 96-well tissue culture plate in the morning. At the end of the day one (6 to 8 h post plating), 100 µL of growth medium from each well were removed and replaced with 100 µL fresh medium.

A 1.0 mg/mL stock solution of LPS, used to induce the expression of COX-2 in the RAW 264.7 cells, was prepared by dissolving 1.0 mg of LPS in 1 mL DMSO. It was vortexed until dissolved and stored at 4° C. Before use, it was melted at room temperature or in a 37° C. water bath.

On day two of the experiment, test materials were prepared as 1000× stock in DMSO. In 1.7 mL microfuge tubes, 1 mL DMEM without FBS was added for test concentrations of 0.05, 0.10, 0.5, and 1.0 µg/mL. Two µL of the 1000×DMSO stock of the test material was added to the 1 mL of medium without FBS. The tube contained the final concentration of the test material concentrated 2-fold and the tube placed in an incubator for 10 minutes to equilibrate to 37° C.

For COX-2 associated PGE$_2$ synthesis, 100 µL of medium were removed from each well of the cell plates prepared on day one and replaced with 100 µL of equilibrated 2× final concentration of the test compounds. Cells were then incubated for 90 minutes. Twenty µL of LPS were added to each well of cells to be stimulated to achieve a final concentration of 1 µg LPS/mL and the cells were incubated for 4 h. The cells were further incubated with 5 µM arachidonic acid for 15 minutes. Twenty-five µL of supernatant medium from each well was transferred to a clean microfuge tube for the determination of PGE$_2$ released into the medium.

Following the LPS stimulation, the appearance of the cells was observed and viability was determined as described in Example 2. No toxicity was observed at the highest concentrations tested for any of the compounds. Twenty-five µL of supernatant medium from each well was transferred to a clean microfuge tube for the determination of PGE$_2$ released into the medium. PGE$_2$ was determined and reported as previously described in Example 1.

For COX-1 associated PGE$_2$ synthesis, 100 µL of medium were removed from each well of the cell plates prepared on day one and replaced with 100 µL of equilibrated 2× final concentration of the test compounds. Cells were then incubated for 90 minutes. Next, instead of LPS stimulation, the cells were incubated with 100 µM arachidonic acid for 15 minutes. Twenty-five µL of supernatant medium from each well was transferred to a clean microfuge tube for the determination of PGE$_2$ released into the medium. The appearance of the cells was observed and viability was determined as described in Example 2. No toxicity was observed at the highest concentrations tested for any of the compounds. Twenty-five µL of supernatant medium from each well was transferred to a clean microfuge tube for the determination of PGE$_2$ released into the medium. PGE$_2$ was determined and reported as previously described in Example 1. The median inhibitory concentrations (IC$_{50}$) for PGE$_2$ synthesis from both COX-2 and COX-1 were calculated as described in Example 2.

TABLE 13

COX-2 and COX-1 inhibition in RAW 264.7 cells by hop fractions and derviatives

| Test Material | COX-2 IC$_{50}$ [µg/mL] | COX-1 IC$_{50}$ [µg/mL] | COX-1/COX-2 |
|---|---|---|---|
| Alpha hop (AA) | 0.21 | 6.2 | 30 |
| Aromahop OE | 1.6 | 4.1 | 2.6 |
| Isohop (IAA) | 0.13 | 18 | 144 |
| Beta acids (BA) | 0.54 | 29 | 54 |
| Hexahop (HHIAA) | 0.29 | 3.0 | 11 |
| Redihop (RIAA) | 0.34 | 29 | 87 |
| Tetrahop (THIAA) | 0.20 | 4.0 | 21 |
| Spent hops (EtOH) | 0.88 | 21 | 24 |

As seen in Table 13, all hops fractions and derivative selectively inhibited COX-2 over COX-1 in this target macrophage model. This was a novel and unexpected finding. The extent of COX-2 selectivity for the hops derivatives IAA and RIIA, respectively, 144- and 87-fold, was unanticipated. Such high COX-2 selectivity combined with low median inhibitory concentrations, has not been previously reported for natural products from other sources.

Example 7

Hops Compounds and Derivatives are Not Direct Cyclooxygenase Enzyme Inhibitors

Summary—This example illustrates that hops compounds and derivatives do not inhibit PGE$_2$ synthesis in A549 pulmonary epithelial cells at physiologically relevant concentrations when tested using the WHMA-COX-2 protocol. Chemicals—Hops and hops derivatives used in this example were previously described.

Cells—A549 (human pulmonary epithelial) Cells were obtained from the American Type Culture Collection (Manassas, Va.) and sub-cultured according to the instructions of the supplier. The cells were routinely cultured at 37° C. with 5% $CO_2$ in RPMI 1640 containing 10% FBS, with 50 units penicillin/mL, 50 μg streptomycin/mL, 5% sodium pyruvate, and 5% L-glutamine. On the day of the experiments, exponentially growing cells were harvested and washed with serum-free RPMI 1640.

Log phase A549 cells were plated at $8 \times 10^4$ cells per well with 0.2 mL growth medium per well in a 96-well tissue culture plate. For the determination of $PGE_2$ inhibition by the test compounds, the procedure of Warner et al. [(1999) Non-steroid drug selectivities for cyclo-oxygenase-1 rather than cyclo-oxygenase-2 are associated with human gastrointestinal toxicity: a full in vitro analysis. Proc Natl Acad Sci USA 96, 7563-7568], also known as the WHMA-COX-2 protocol was followed with no modification. Briefly, 24 hours after plating of the A549 cells, interleukin-IB (10 ng/mL) was added to induce the expression of COX-2. After 24 hr, the cells were washed with serum-free RPMI 1640 and the test materials, dissolved in DMSO and serum-free RPMI, were added to the wells to achieve final concentrations of 25, 5.0, 0.5 and 0.05 μg/mL. Each concentration was run in duplicate. DMSO was added to the control wells in an equal volume to that contained in the test wells. Sixty minutes later, A23187 (50 μM) was added to the wells to release arachidonic acid. Twenty-five μL of media were sampled from the wells 30 minutes later for $PGE_2$ determination.

Cell viability was assessed. No toxicity was observed at the highest concentrations tested for any of the compounds. $PGE_2$ in the supernatant medium was determined and reported.

The median inhibitory concentration ($IC_{50}$) for $PGE_2$ synthesis was calculated.

Results—At the doses tested, the experimental protocol failed to capture a median effective concentration of any of the hops extracts or derivatives. Since the protocol requires the stimulation of COX-2 expression prior to the addition of the test compounds, the likely answer to the failure of the test materials to inhibit $PGE_2$ synthesis is that their mechanism of action is to inhibit the expression of the COX-2 isozyme and not activity directly. While some direct inhibition can be observed using the WHMA-COX-2 protocol, this procedure is inappropriate in evaluating the anti-inflammatory properties of hops compounds or derivatives of hops compounds.

Example 8

Lack of Inhibition of $PGE_2$ Synthesis in Gastric Mucosal Cells by Hops (*Humulus lupulus*) Compounds and Derviatives Summary—This example illustrates the lack of $PGE_2$ inhibition by hops fractions and in the AGS human gastric mucosal cell line implying low gastric irritancy potential of these compounds.

AGS cells were grown and used for testing hops compounds and derivatives. $PGE_2$ was determined and reported as previously described in Example 1. The median inhibitory concentrations ($IC_{50}$) for $PGE_2$ synthesis from AGS cells were calculated.

TABLE 14

Lack of $PEG_2$ inhibition in AGS gastric mucosal cells by hop fraction and dreivatives

| Test Material | $IC_{50}$ AGS [μg/mL] |
|---|---|
| Alpha hop (AA) | >25 |
| Aromahop OE | >25 |
| Isohop (IAA) | >25 |
| Beta acids (BA) | >25 |
| Hexahop (HHIAA) | >25 |
| Redihop (RIAA) | >25 |
| Tetrahop (THIAA) | >25 |
| Spent hops (EtOH) | >25 |

As seen in Table 14, all hops fractions and derivatives were unable to inhibit $PGE_2$ synthesis by 50% or more at the highest concentrations tested in the AGS gastric mucosal cell line. Based on the anti-inflammatory potency exhibited by these fractions in target macrophages, this was a novel and unexpected finding.

Example 9

Mite Dust Allergens Activate $PGE_2$ Biosynthesis in A549 Pulmonary Cells

Summary—This example illustrates that house mite dust allergens can induce $PGE_2$ biosynthesis in pulmonary epithelial cells.

Background

Sensitivity to allergens is a problem for an increasing number of consumers. This issue has been complicated by a surprising increase in asthma over the past few years. Asthma suffers are especially sensitive to airborne allergens. Allergy rates are also on the rise. This gives rise to increased awareness of the causes of allergy symptoms and how to decrease the associated discomfort. Approximately 10% of the population become hypersensitized (allergic) upon exposure to antigens from a variety of environmental sources. Those antigens that induce immediate and/or delayed types of hypersensitivity are known as allergens. These include products of grasses, trees, weeds, animal dander, insects, food, drugs, and chemicals. Genetic predisposition of an individual is believed to play a role in the development of immediate allergic responses such as atopy and anaphylaxis whose symptoms include hay fever, asthma, and hives.

Many allergens are protein-based molecules, and these protein allergens can originate from many sources. It has been know for some time that one of the most common sources of allergens in a house is from dust mites. Of course, as is the case with all allergens, only certain people are allergic to dust mite allergens. But this group of people can be quite large in many areas, especially in hot humid areas. For example, in the southeastern United States of America, where it is both hot and humid for much of the year, the incidence of house dust mite allergies in the general population can be as high as 25%. House dust mites thrive in plush carpets, overstuffed upholstery, cushy bed comforters and the like.

Methods

Mite dust allergen isolation—*Dermatophagoides farinae* are the American house dust mite. *D. farinae* were cultured on a 1:1 ratio of Purina Laboratory Chow (Ralston Purina, Co, St. Louis, Mo.) and Fleischmann's granulated dry yeast (Standard Brands, Inc. New York, N.Y.) at room temperature and 75% humidity. Live mites were aspirated from the culture container as they migrated from the medium, killed by freezing, desiccated and stored at 0% humidity. The allergenic component of the mite dust was extracted with water at ambient temperature. Five-hundred mg of mite powder were added to 5 mL of water (1:10 w/v) in a 15 mL conical centrifuge tube (VWR, Rochester, N.Y.), shaken for one minute and allowed to stand overnight at ambient temperature. The next day, the aqueous phase was filtered using a 0.2 µm disposable syringe filter (Nalgene, Rochester, N.Y.). The filtrate was termed mite dust allergen and used to test for induction of $PGE_2$ biosynthesis in A549 pulmonary epithelial cells.

Cell culture and treatment—This experiment involved the human airway epithelial cell line, A549 (American Type Culture Collection, Bethesda, Md.). The cells were cultured and treated. Mite allergen was added to the culture medium to achieve a final concentration of 1000 ng/mL. Twenty-four hours later, the culture medium was sampled for $PGE_2$ concentration.

$PGE_2$ assay—Determination of $PGE_2$ in the culture medium was performed as previously described in Example 1.

Statistical analysis—Means of eight replicates per treatment were computed using Excel® spreadsheets (Microsoft, Redmond, Wash.).

Results

Figure 2:
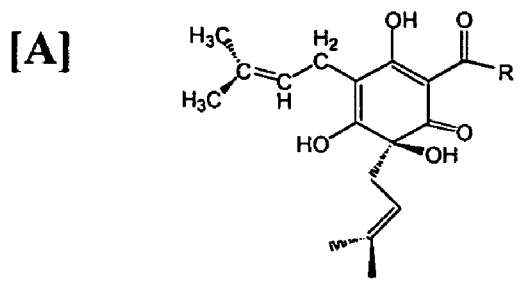
FIG. 2 illustrates [A] the alpha-acid genus (AA) and representative species humulone (R=—$CH_2CH(CH_3)_2$), cohumulone (R=—$CH(CH_3)_2$), and adhumulone (R=—$CH(CH_3)CH_2CH_3$); [B] the isoalpha acid genus (IAA) and representative species isohumulone (R=—$CH_2CH(CH_3)_2$), isocohumulone (R=—$CH(CH_3)_2$), and isoadhumulone (R=—$CH(CH_3)CH_2CH_3$); [C] the reduced isomerized isoalpha acid genus (RIAA) and representative species dihydro-isohumulone (R=—$CH_2CH(CH_3)_2$) dihydro-isocohumulone (R=, —$CH(CH_3)_2$), and dihydro-isoadhumulone (R=—$CH(CH_3)CH_2CH_3$); [D] the tetra-hydroisoalpha acid genus (THIAA) and representative species tetra-hydro-isohumulone (R=—$CH_2CH(CH_3)_2$), tetra-hydro-isocohumulone ((R=, —$CH(CH_3)_2$), and tetra-hydro-isoadhumulone (R=—$CH(CH_3)CH_2CH_3$); [E] and the hexa-hydroisoalpha acid (HHIAA) genus with representative species hexa-hydro-isohumulone (R=—$CH_2CH(CH_3)_2$) hexa-hydro-isocohumulone (R=—$CH(CH_3)_2$), and hexa-hydro-isoadhumulone (R=—$CH(CH_3)CH_9CH_3$).
Figure 2:
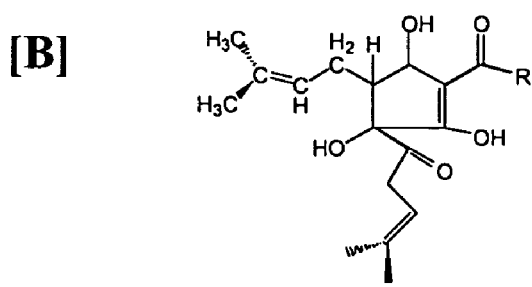
Figure 2:
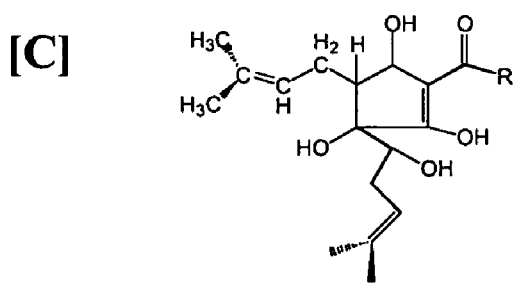
Figure 2:
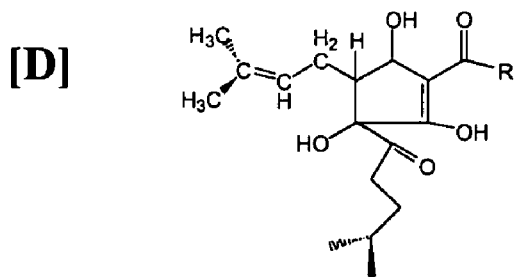
Figure 2:
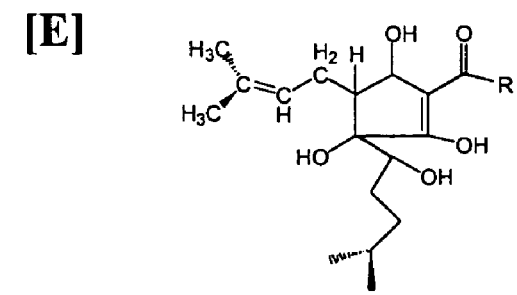

Mite allergen treatment increased $PGE_2$ biosynthesis 6-fold in A549 cells relative to the solvent treated controls (FIG. 2).

Example 10

Hops Derivatives Inhibit Mite Dust Allergen Activation of $PGE_2$ Biosynthesis in A549 Pulmonary Cells Summary—This example illustrates that hops derivatives are capable of inhibiting the $PGE_2$ stimulatory effects of mite dust allergens in A549 pulmonary cells.

Methods

The cell line and testing procedures are as described in Example 9. In addition to mite dust allergen, test materials included Hops fractions (1) alpha hop (1% alpha acids; AA), (2) aromahop OE (10% beta acids and 2% isomerized alpha acids, (3) isohop (isomerized alpha acids; IAA), (4) beta acid solution (beta acids BA), (5) hexahop gold (hexahydro isomerized alpha acids; HHIAA), (6) redihop (reduced isomerized-alpha acids; RIAA), and (7) tetrahop (tetrahydro-iso-alpha acids THIAA). Test materials at a final concentration of 10 µg/mL were added 60 minutes prior to the addition of the mite dust allergen.

Results

Table 15 depicts the extent of inhibition of $PGE_2$ biosynthesis by hops derivatives in A549 pulmonary cells stimulated by mite dust allergen. All hops derivatives were capable of significantly inhibiting the stimulatory effects of mite dust allergens.

TABLE 15

$PGE_2$ inhibition by hops derviatives in A549 pulmonary epithelial cells stimulated by mite dust allergen

| Test Material | Percent Inhibition of $PGE_2$ Biosynthesis |
|---|---|
| Alpha hop (AA) | 81 |
| Aromahop OE | 84 |
| Isohop (IAA) | 78 |
| Beta acids (BA) | 83 |
| Hexahop (HHIAA) | 82 |
| Redihop (RIAA) | 81 |
| Tetrahop (THIAA) | 76 |

In conclusion, it would also be useful to identify a natural formulation of compounds that would inhibit expression of COX-2, inhibit prostaglandin synthesis selectively in target cells, or inhibit inflammation response selectively in target cells.

A preferred embodiment comprises compositions containing at least one fraction isolated or derived from hops (*Humulus lupulus*). Examples of fractions isolated or derived from hops are alpha acids, isoalpha acids, reduced isoalpha acids, tetra-hydroisoalpha acids, hexa-hydroisoalpha acids, beta acids, and spent hops. Preferred compounds of fractions isolated or derived from hops, include, but are not limited to, humulone, cohumulone, adhumulone, isohumulone, isocohumulone, isoadhumulone, dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone. Preferred compounds can also bear substituents, such as halogens, ethers, and esters. Another embodiment comprises composition containing tryptanthrin and conjugates thereof.

Other embodiments relate to combinations of components. One embodiment relates to compositions that include, as a first component, an active ingredient isolated or derived from an extract of hops and as a second component at least one member selected from the group consisting of rosemary (*Rosmarinus officinalis* L.), an extract or compound derived from rosemary, a triterpene species or derivatives or conjugates thereof, and tryptanthrin or conjugates thereof. Another embodiment relates to compositions that include, as a first component, tryptanthrin or conjugates thereof and as a second component at least one member selected from the group consisting of an active ingredient isolated or derived from an extract of hops, rosemary, an extract or compound derived from rosemary, and a triterpene species or derivatives or conjugates thereof.

It will be readily apparent to those skilled in the art that various changes and modifications of an obvious nature may be made without departing from the spirit of the invention, and all such changes and modifications are considered to fall within the scope of the invention as defined by the appended claims. Such changes and modifications would include, but not be limited to, the incipient ingredients added to affect the capsule, tablet, lotion, food or bar manufacturing process as well as vitamins, herbs, flavorings and carriers. Other such changes or modifications would include the use of other herbs or botanical products containing the combinations of the preferred embodiments disclosed above. Many additional modifications and variations of the embodiments described herein may be made without departing from the scope, as is apparent to those skilled in the art. The specific embodiments described herein are offered by way of example only.

What is claimed is:

1. A method of treating an autoimmune disease comprising a step of administering to a mammal in need thereof a therapeutically effective amount of a composition comprising a compound selected from the group consisting of dihydro-isohumulone, dihydro-isocohumulone, dihydro-isoadhumulone, tetrahydro-isohumulone, tetrahydro-isocohumulone, tetrahydro-isoadhumulone, hexahydro-isohumulone, hexahydro-isocohumulone, and hexahydro-isoadhumulone, a mineral, and a vitamin.

2. The method of claim 1, wherein the autoimmune disease is selected from the group consisting of Crohn's disease, Raynaud's Phenomenon, rheumatoid arthritis, and systemic lupus erythematosus.

3. The method of claim 1, wherein the mineral is selected from the group consisting of calcium, selenium, zinc, copper, iron, chromium, magnesium, manganese, vanadium, molybdenum, and boron.

4. The method of claim 1, wherein the vitamin is selected from the group consisting of Vitamin A, Vitamin B, Vitamin C, Vitamin D, Vitamin E, Vitamin K, biotin, folate, pantothenic acid, para-aminobenzoic acid, and betaine.

5. The method of claim 1, wherein the composition comprises about 0.5 to 10,000 mg of the compound.

6. The method of claim 1, wherein the composition comprises about 50 to 7,500 mg of the compound.

7. The method of claim 1, wherein the composition further comprises a pharmaceutically acceptable carrier.

8. The method of claim 1, wherein the composition is administered orally, topically, parenterally, or rectally.

* * * * *